United States Patent
Li et al.

(10) Patent No.: US 10,654,794 B2
(45) Date of Patent: May 19, 2020

(54) FUSED TRICYCLIC Γ-AMINO ACID DERIVATIVE, PREPARATION METHOD THEREFOR, AND MEDICAL USE THEREOF

(71) Applicant: SICHUAN HAISO PHARMACEUTICAL CO., LTD., Wenjiang District, Chengdu (CN)

(72) Inventors: Yao Li, Chengdu (CN); Zongjun Shi, Chengdu (CN); Bo Xu, Chengdu (CN)

(73) Assignee: SICHUAN HAISO PHARMACEUTICAL CO., LTD., Chengdu (CN)

( * ) Notice: Subject to any disclaimer, the term of this patent is extended or adjusted under 35 U.S.C. 154(b) by 0 days.

(21) Appl. No.: 16/330,847

(22) PCT Filed: Sep. 12, 2017

(86) PCT No.: PCT/CN2017/101364
§ 371 (c)(1),
(2) Date: Mar. 6, 2019

(87) PCT Pub. No.: WO2018/050046
PCT Pub. Date: Mar. 22, 2018

(65) Prior Publication Data
US 2019/0218172 A1     Jul. 18, 2019

(30) Foreign Application Priority Data
Sep. 14, 2016 (CN) .......... 2016 1 0825611

(51) Int. Cl.
| | |
|---|---|
| C07C 229/50 | (2006.01) |
| C07C 229/28 | (2006.01) |
| C07C 309/29 | (2006.01) |
| A61P 29/00 | (2006.01) |
| A61P 25/06 | (2006.01) |
| A61P 25/04 | (2006.01) |
| A61P 25/00 | (2006.01) |
| A61K 31/195 | (2006.01) |
| A61K 45/06 | (2006.01) |

(52) U.S. Cl.
CPC .......... *C07C 229/50* (2013.01); *A61K 31/195* (2013.01); *A61K 45/06* (2013.01); *A61P 25/00* (2018.01); *A61P 25/04* (2018.01); *A61P 25/06* (2018.01); *A61P 29/00* (2018.01); *C07C 229/28* (2013.01); *C07C 309/29* (2013.01); *Y02P 20/55* (2015.11)

(58) Field of Classification Search
CPC ... C07C 229/50; C07C 229/28; C07C 309/29; A61K 31/195; A61P 25/00
See application file for complete search history.

(56) References Cited

U.S. PATENT DOCUMENTS 7,947,738 B2 *  5/2011  Shimada ............... C07C 323/58
                                                                514/561

FOREIGN PATENT DOCUMENTS

| CN | 1720219 | 1/2006 |
|---|---|---|
| CN | 101878193 | 11/2010 |
| GB | 2374595 | 10/2002 |
| JP | 2010-079668 | 4/2010 |
| WO | WO 2009/041453 | 4/2009 |
| WO | WO 2010/079668 | 7/2010 |
| WO | WO 2017/107907 | 6/2017 |

OTHER PUBLICATIONS

Wikipedia, Wikipedia, Cocrystal, 2019, pp. 1-7, recovered from internet on Oct. 9, 2019 from https://en.wikipedia.org/wiki/ Cocrystal. (Year: 2019).*
Hursthouse et al, Organic Process Research & Development, Why Do Organic Compounds Crystallise Well or Badly or Ever so Slowly? Why is Crystallisation Nevertheless Such a Good Purification Technique?, 2009, 73, pp. 1231-1240. (Year: 2009).*
Lu el (Annual Reviews in Biochemistry, Metabolite Measurement: Pitfalls to Avoid and Practices to Follow, 2017 , 86, pp. 277-304, numbered 1-34 in Author Manuscript. (Year: 2017).*
Geisel et al (Helvetica Chimica Acta, 1973, 56(3), pp. 1046-1055. (Year: 1973).*
International Search Report, PCT/CN2017/101364 (dated Dec. 1, 2017).
First Office Action + Search Report, TW App. No. 106131443 (dated Jan. 8, 2019).
Geisel, M.et al.,Die Cyclopropylcarbinyl-Cyclobutyl-Homoallyl-Umlagerung.I.Teil.Synthese von Tricyclo[3.2.1.0 2, 7]octan-3-ol, endo-und exo-Tri-cyclo [3.2.1.0 3, 6]octan-4-ol und exo-Bicyclo [3.2.1]-oct-2-en-7-ol, Helvetica Chimica Acta, 56(3), Dec. 31, 1973,pp. 1046-1055.

(Continued)

*Primary Examiner* — Paul A Zucker
(74) *Attorney, Agent, or Firm* — Foley & Lardner LLP

(57) ABSTRACT

Disclosed are a fused tricyclic γ-amino acid derivative and a medical use thereof, in particular, the present invention relates to a fused cyclic γ-amino acid derivative as shown in general formula (I), or a stereoisomer, solvate, metabolite, prodrug, pharmaceutically acceptable salt or eutectic thereof, a pharmaceutical composition containing same, and the use of a compound or the composition in the field of analgesia, wherein the definitions of each substituent in general formula (I) are the same as the definitions in the description.

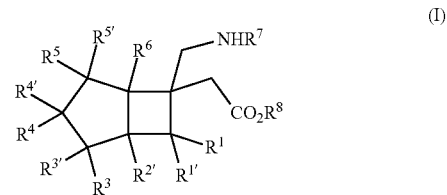

18 Claims, 1 Drawing Sheet

(56) References Cited

OTHER PUBLICATIONS

Yates, P. et al., Decomposition of I-Diazo-3-(2, 2, 3-Trimethylcyclo-Pent-3-Enyl)Propan-2-One. A Novel Synthesis and Rearrangement of a Tricyclo[3.2. 1.0 3, 6] Octan-4-One, Tetrahedron Letters, No. 20, Dec. 31, 1968, pp. 2493-2496.
Parisi, L., et al., "Afterdischarge Activity in Neuropathic Patients with Frequent Muscle Cramps," Acta. Neurol. Scand., 102, pp. 359-362 (2000).
Blommel, M., et al., "Pregabalin: An Antiepileptic Agent Useful for Neuropathic Pain," Am J Health Syst Pharm., 64(14):1475-1482 (Jul. 15, 2007).
Felix, R., et al., "Dissection of Functional Domains of the Voltage-Dependent $Ca^{2+}$ Channel $\alpha_2\delta$ Subunit," J. Neuroscience, 17, 6884-6891 (Sep. 15, 1997).
Hobom, M., et al., "Neuronal Distribution and Functional Characterization of the Calcium Channel $\alpha_2\delta$-2 Subunit," Eur. J. Neuroscience, 12, pp. 1217-1226 (2000).
Klugbauer, N., et al., "Molecular Diversity of the Calcium Channel $\alpha_2\delta$ Subunit," J. Neuroscience, 19, pp. 684-691 (Jan. 15, 1999).
Qin, N., et al., "Molecular Cloning and Characterization of the Human Voltage-Gated Calcium Channel $\alpha_2\delta$-4 Subunit," Mol. Pharmacol., vol. 62, No. 8, pp. 485-496 (2002).

\* cited by examiner

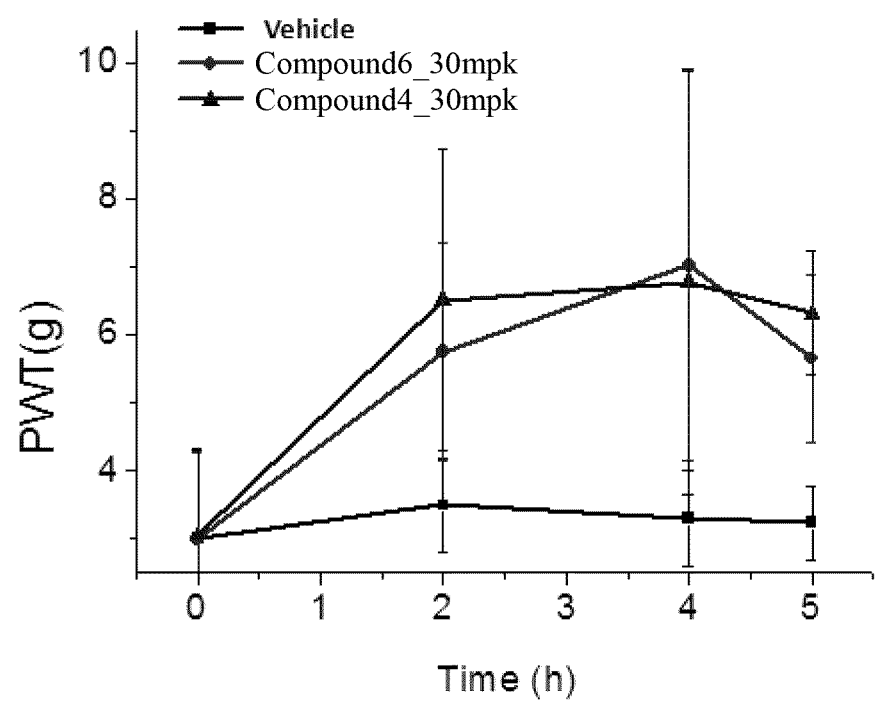

FUSED TRICYCLIC Γ-AMINO ACID DERIVATIVE, PREPARATION METHOD THEREFOR, AND MEDICAL USE THEREOF

CROSS-REFERENCE TO RELATED APPLICATIONS

This application is a National Stage Application of PCT/CN2017/101364, filed Sep. 12, 2017, which claims the benefit of and priority to Chinese Patent Application No. 201610825611.9, filed Sep. 14, 2016, the entire contents of which are incorporated herein by reference.

TECHNICAL FIELD

The present invention relate to a fused tricyclic γ-amino acid derivative represented by general formula (I), or a stereoisomer, a solvate, a prodrug, a metabolite, a pharmaceutically acceptable salt, or a cocrystal thereof, a pharmaceutical composition comprising the same, and analgesic use thereof.

BACKGROUND ART

The voltage-gated calcium channels consist of an al subunit and auxiliary subunits α2δ, β, and γ. The α2δ subunit can regulate the density and voltage-dependent kinetics of the calcium channels (Felix et al., (1997) J. Neuroscience 17: 6884-6891; Klugbauer et al., (1999) J. Neuroscience 19:684-691; Hobom et al., (2000) Eur. J. Neuroscience 12: 1217-1226; and Qin et al., (2002) Mol. Pharmacol. 62:485-496). It has been demonstrated that compounds having a high affinity for the voltage-dependent calcium channel subunit α2δ, such as pregabalin and gabapentin, may be effective in the treatment of pain. In mammals, the α2δ subunit has four subtypes, each encoded by a different gene. α2δ subtype 1 and subtype 2 show a high affinity for pregabalin, while α2δ subtype 3 and subtype 4 do not have a significant binding capacity to a drug.

However, for gabapentin, the proportion of patients with diabetic peripheral neuropathy whose pain is relieved to a great extent by using gabapentin is approximately 60% (Acta Neurol. Scand. 101:359-371, 2000), while for pregabalin, although it is better tolerated than gabapentin, it is less safe and may be abused or induce drug dependence in patients (Am J Health Syst Pharm. 2007; 64(14): 1475-1482).

In view of the limitations of gabapentin and pregabalin, there is a need for developing new compounds having better efficacy.

SUMMARY OF INVENTION

An objective of the present invention is to provide a structurally novel, highly efficacious fused tricyclic γ-amino acid derivative, or a stereoisomer, a solvate, a metabolite, a pharmaceutically acceptable salt, a cocrystal, or a prodrug thereof, a pharmaceutical composition comprising the same, and analgesic use thereof.

The present invention relates to a compound represented by general formula (I), or all stereoisomers, solvates, prodrugs, metabolites, pharmaceutically acceptable salts or cocrystals thereof,

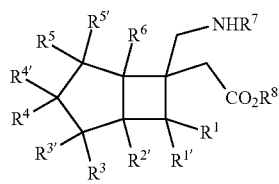

wherein
$R^1$ and $R^4$ bond each other to form $—(CR^9R^{9'})_n—$ or $—CR^9=CR^{9'}—$;
$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, amino, carboxy, carboxylate, amide group, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl, wherein the alkyl, alkoxy, sulfanyl, alkenyl, alkynyl, carbocyclyl or heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl, and the heterocyclyl contains 1 to 2 heteroatoms selected from N, O or S;
n is selected from 1, 2 or 3;
alternatively, any pair of $R^3$ and $R^{3'}$, $R^5$ and $R^{5'}$, and $R^9$ and $R^{9'}$ forms

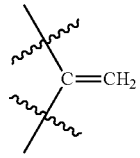 [SMILES: *C(*)=C]

together with the carbon atom to which they are attached, and the

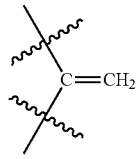

is optionally further substituted with 0 to 2 substituents selected from F, Cl, Br, I, a $C_{1-6}$ alkyl, a 3- to 6-membered carbocyclyl or a 3- to 6-membered heterocyclyl, wherein the alkyl, 3- to 6-membered carbocyclyl or 3- to 6-membered heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl;
alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, amino, carboxy, a $C_{1-6}$ alkyl, a $C_{1-6}$ alkoxy, or a $C_{1-6}$ sulfanyl;
$R^7$ is selected from H, a $C_{1-6}$ alkyl, or an amino-protecting group; and
$R^8$ is selected from H, a $C_{1-6}$ alkyl, or a carboxy-protecting group.

It is to be understood that, the expression "any pair of $R^3$ and $R^{3'}$, $R^5$ and $R^{5'}$, and $R^9$ and $R^{9'}$ forms

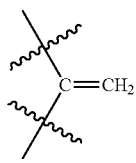

together with the carbon atom to which they are attached" according to the present invention means that $R^3$ and $R^{3'}$ together with the carbon atom to which they are attached form

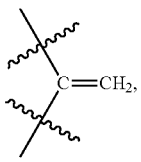

$R^5$ and $R^{5'}$ together with the carbon atom to which they are attached form

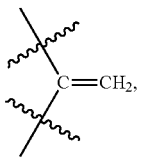 [SMILES: *C(*)=C]

or $R^9$ and $R^{9'}$ together with the carbon atom to which they are attached form

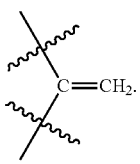 [SMILES: *C(*)=C]

A preferred embodiment of the present invention provides a compound represented by general formula (I), or all stereoisomers, solvates, metabolites, pharmaceutically acceptable salts, cocrystals, or prodrugs thereof, wherein $R^1$ and $R^4$ bond each other to form $-(CR^9R^{9'})_n-$ or $-CR^9=CR^{9'}-$;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, amino, carboxy, carboxylate, amide group, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl; preferably, $R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, hydroxyl, amino, carboxy, carboxylate, amide group, a $C_{1-4}$ alkyl, a $C_{1-4}$ alkoxy, a $C_{1-4}$ sulfanyl, a $C_{2-4}$ alkenyl, a $C_{2-4}$ alkynyl, or a 3- to 6-membered carbocyclyl; more preferably, $R^{1'}$, $R^2$, $R^3$, $R^{3'}$, $R^{4'}$, $R^5$, $R^{5'}$, $R^6$, $R^9$ or $R^{9'}$ is each independently selected from H, F, hydroxyl, methyl, ethyl, propyl, butyl, methoxy, ethoxy, propoxy, butoxy, methylthio, ethylthio, vinyl, propenyl, allyl, ethynyl, propynyl, propargyl, cyclopropyl, cyclobutyl, cyclopentyl or cyclohexyl; wherein the alkyl, alkoxy, sulfanyl, alkenyl, alkynyl, carbocyclyl, heterocyclyl, methyl, ethyl, propyl, butyl, methoxy, ethoxy, propoxy, butoxy, methylthio, ethylthio, vinyl, propenyl, allyl, ethynyl, propynyl, propargyl, cyclopropyl, cyclobutyl, cyclopentyl or cyclohexyl is optionally further substituted with 0 to 6 substituents selected from F, Cl, Br, I, hydroxyl, a $C_{1-6}$ alkyl, or a 3- to 6-membered carbocyclyl, and the heterocyclyl contains 1 to 2 heteroatoms selected from N, O or S;

n is selected from 1, 2 or 3, preferably 1 or 2;

alternatively, any pair of $R^3$ and $R^{3'}$, $R^5$ and $R^{5'}$, and $R^9$ and $R^{9'}$ forms

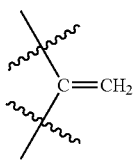 [SMILES: *C(*)=C]

together with the carbon atom to which they are attached, and the

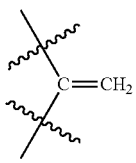

is optionally further substituted with 0 to 2 substituents selected from F, Cl, Br, I, hydroxyl, a $C_{1-6}$ alkyl, a $C_{1-6}$ alkyl substituted with 1 to 3 halogen atoms selected from F, Cl or Br, or a 3- to 6-membered carbocyclyl, or is preferably further substituted with 0 to 2 substituents selected from F, Cl, Br, I, hydroxyl, methyl, ethyl, propyl, $CH_2F$, $CHF_2$, $CF_3$, $CH_2CH_2F$, $CHFCH_3$, $CHFCH_2F$, $CH_2CF_3$, $CH_2CH_2CH_2F$, cyclopropyl, cyclobutyl, cyclopentyl or cyclohexyl;

alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, amino, carboxy, a $C_{1-6}$ alkyl, a $C_{1-6}$ alkoxy, or a $C_{1-6}$ sulfanyl, preferably further substituted with 0 to 4 substituents selected from F, Cl, Br, I, hydroxyl, amino, methyl, ethyl, propyl, butyl, methoxy, ethoxy, propoxy, methylthio, and ethylthio;

$R^7$ is selected from H, a $C_{1-6}$ alkyl, or an amino-protecting group, preferably H, methyl, ethyl, propyl, butyl, or an amino-protecting group, wherein the amino-protecting group is preferably $C_{1-6}$ alkoxycarbonyl, $C_{1-6}$ alkylacyl, $C_{6-10}$ arylacyl, $C_{3-15}$ cycloalkyloxycarbonyl, $C_{6-10}$ arylmethylene, $C_{3-10}$ heteroarylmethylene, benzyl, trityl or phthaloyl, where the alkoxycarbonyl, alkylacyl, arylacyl, cycloalkyloxycarbonyl, arylmethylene or heteroarylmethylene is optionally further substituted with 0 to 5 substituents selected from F, Cl, Br, I, hydroxyl, nitro, cyano, a $C_{1-6}$ alkyl, a $C_{1-6}$ alkoxy or a 3- to 15-membered carbocyclyl; and is more preferably formyl, acetyl, phenylacyl, methoxycarbonyl, ethoxycarbonyl, propoxycarbonyl, t-butoxy carbonyl, benzyloxycarbonyl, phenoxycarbonyl, 9-fluorenylmethoxycarbonyl, adamantyloxycarbonyl, benzylcarbonyl, benzyl, trityl or phthaloyl; and $R^8$ is selected from H, a $C_{1-6}$ alkyl, or a carboxy-protecting group, preferably H, methyl, ethyl, propyl, butyl, or a carboxy-protecting group, wherein the carboxy-protecting group is preferably a $C_{1-6}$ alkyl, benzyl, $C_{1-6}$ alkyl-(=O)O—$C_{1-6}$ alkyl-, $C_{1-6}$ alkyl-O(=O)—$C_{1-6}$ alkyl-, $(C_{1-6}$ alkyl$)_3$ silyl, (2-methylthio)ethyl, 3-methyl-2-butenyl, 5-indanyl or 3-2-benzo[C]furanonenyl, more preferably methyl, ethyl, n-propyl, isopropyl, n-butyl, sec-butyl, neobutyl, t-butyl, n-pentyl, isopentyl, neopentyl, n-hexyl, trichloroethyl, benzyl, p-nitrobenzyl, o-nitrobenzyl, p-methoxybenzyl, p-t-butylbenzyl, acetoxymethyl, propionyloxymethyl, butyryloxymethyl, isobutyryloxymethyl, pentoxymethyl, pivaloyloxymethyl, acetoxyethyl, acetoxypropyl, acetoxybutyl, propionyloxyethyl, propionyloxypropyl, butyryloxyethyl, isobutyryloxyethyl, pivaloyloxyethyl, hexanoyloxyethyl, isobutyryloxymethyl, ethylbutyryloxymethyl, dimethylbutyryloxymethyl, pentanoyloxyethyl, methoxycarbonyloxymethyl, ethoxycarbonyloxymethyl, propoxycarbonyloxyethyl, isopropoxycarbonyloxyethyl, t-butoxycarbonyloxymethyl, methoxycarbonyloxyethyl, ethoxycarbonyloxyethyl, isopropoxycarbonyloxyethyl, t-butyl(dimethyl)silyl, trimethylsilyl, methoxymethyl, ethoxymethyl, propoxymethyl, isopropoxymethyl, (2-methylthio)ethyl, 3-methyl-2-butenyl, 5-indanyl and 3-2-benzo[C]furanonenyl.

A preferred embodiment of the present invention provides a compound represented by general formula (Ia) or (Ib), or all stereoisomers, solvates, metabolites, pharmaceutically acceptable salts, cocrystals, or prodrugs thereof,

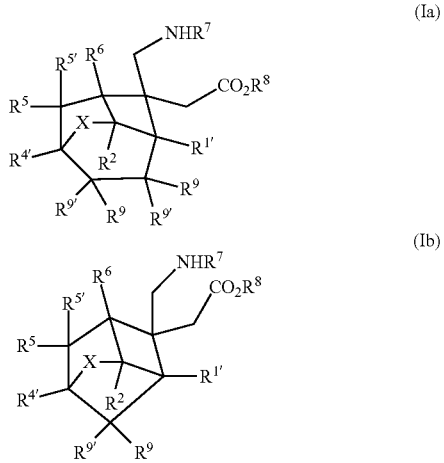

wherein
X represents $CR^3R^{3'}$;
$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl; preferably $R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, hydroxyl, a $C_{1-4}$ alkyl, a $C_{1-4}$ alkoxy, a $C_{1-4}$ sulfanyl, a $C_{2-4}$ alkenyl, a $C_{2-4}$ alkynyl, or a 3- to 6-membered carbocyclyl; more preferably, $R^{1'}$, $R^2$, $R^3$, $R^{3'}$, $R^{4'}$, $R^5$, $R^{5'}$, $R^6$, $R^9$ or $R^{9'}$ is each independently selected from H, F, hydroxyl, methyl, ethyl, propyl, butyl, methoxy, ethoxy, propoxy, butoxy, methylthio, ethylthio, vinyl, propenyl, allyl, ethynyl, propynyl, propargyl, cyclopropyl, cyclobutyl, cyclopentyl or cyclohexyl; wherein the alkyl, alkoxy, sulfanyl, alkenyl, alkynyl, carbocyclyl, heterocyclyl, methyl, ethyl, propyl, butyl, methoxy, ethoxy, propoxy, butoxy, methylthio, ethylthio, vinyl, propenyl, allyl, ethynyl, propynyl, propargyl, cyclopropyl, cyclobutyl, cyclopentyl or cyclohexyl is optionally further substituted with 0 to 6 substituents selected from F, Cl, Br, I, hydroxyl, a $C_{1-6}$ alkyl, or a 3- to 6-membered carbocyclyl, and the heterocyclyl contains 1 to 2 heteroatoms selected from N, O or S;

alternatively, any pair of $R^3$ and $R^{3'}$, $R^5$ and $R^{5'}$, and $R^9$ and $R^{9'}$ forms

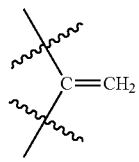 [SMILES: *C(*)=C]

together with the carbon atom to which they are attached, and the

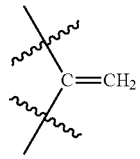

is optionally further substituted with 0 to 2 substituents selected from F, Cl, Br, I, hydroxyl, a $C_{1-6}$ alkyl, a $C_{1-6}$ alkyl substituted with 1 to 3 halogen atoms selected from F, Cl or Br, a 3- to 6-membered carbocyclyl or a 3- to 6-membered heterocyclyl, or is preferably further substituted with 0 to 2 substituents selected from F, Cl, Br, I, hydroxyl, methyl, ethyl, propyl, $CH_2F$, $CHF_2$, $CF_3$, $CH_2CH_2F$, $CHFCH_3$, $CHFCH_2F$, $CH_2CF_3$, $CH_2CH_2CH_2F$, cyclopropyl, cyclobutyl, cyclopentyl or cyclohexyl;

alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, a $C_{1-6}$ alkyl, a $C_{1-6}$ alkoxy or a $C_{1-6}$ sulfanyl, preferably further substituted with 0 to 4 substituents selected from F, Cl, Br, I, hydroxyl, methyl, ethyl, propyl, butyl, methoxy, ethoxy, propoxy, methylthio, and ethylthio;

$R^7$ is selected from H, a $C_{1-6}$ alkyl, or an amino-protecting group, preferably H, methyl, ethyl, propyl, butyl, or an amino-protecting group, wherein the amino-protecting group is preferably $C_{1-6}$ alkoxycarbonyl, $C_{1-6}$ alkylacyl, $C_{6-10}$ arylacyl, $C_{3-15}$ cycloalkyloxycarbonyl, $C_{6-10}$ arylmethylene, $C_{3-10}$ heteroarylmethylene, benzyl, trityl or phthaloyl, where the alkoxycarbonyl, alkylacyl, arylacyl, cycloalkyloxycarbonyl, arylmethylene or heteroarylmethylene is optionally further substituted with 0 to 5 substituents selected from F, Cl, Br, I, hydroxyl, nitro, cyano, a $C_{1-6}$ alkyl, a $C_{1-6}$ alkoxy or a 3- to 15-membered carbocyclyl; and is more preferably formyl, acetyl, phenylacyl, methoxycarbonyl, ethoxycarbonyl, propoxycarbonyl, t-butoxy carbonyl, benzyloxycarbonyl, phenoxycarbonyl, 9-fluorenylmethoxycarbonyl, adamantyloxycarbonyl, benzylcarbonyl, benzyl, trityl or phthaloyl; and $R^8$ is selected from H, a $C_{1-6}$ alkyl, or a carboxy-protecting group, preferably H, methyl, ethyl, propyl, butyl, or a carboxy-protecting group, wherein the carboxy-protecting group is preferably a $C_{1-6}$ alkyl, benzyl, $C_{1-6}$ alkyl-(=O) O—$C_{1-6}$ alkyl-, $C_{1-6}$ alkyl-O(=O)—$C_{1-6}$ alkyl-, ($C_{1-6}$ alkyl)$_3$ silyl, (2-methylthio)ethyl, 3-methyl-2-butenyl, 5-indanyl or 3-2-benzo[C]furanonenyl, more preferably methyl, ethyl, n-propyl, isopropyl, n-butyl, sec-butyl, neobutyl, t-butyl, n-pentyl, isopentyl, neopentyl, n-hexyl, trichloroethyl, benzyl, p-nitrobenzyl, o-nitrobenzyl, p-methoxybenzyl, p-t-butylbenzyl, acetoxymethyl, propionyloxymethyl, butyryloxymethyl, isobutyryloxymethyl, pentoxymethyl, pivaloyloxymethyl, acetoxyethyl, acetoxypropyl, acetoxybutyl, propionyloxyethyl, propionyloxypropyl, butyryloxyethyl, isobutyryloxyethyl, pivaloyloxyethyl, hexanoyloxyethyl, isobutyryloxymethyl, ethylbutyryloxymethyl, dimethylbutyryloxymethyl, pentanoyloxyethyl, methoxycarbonyloxymethyl, ethoxycarbonyloxymethyl, propoxycarbonyloxyethyl, isopropoxycarbonyloxyethyl, t-butoxycarbonyloxymethyl, methoxycarbonyloxyethyl, ethoxycarbonyloxyethyl, isopropoxycarbonyloxyethyl, t-butyl(dimethyl)silyl, trimethylsilyl, methoxymethyl, ethoxymethyl, propoxymethyl, isopropoxymethyl, (2-methylthio)ethyl, 3-methyl-2-butenyl, 5-indanyl and 3-2-benzo[C]furanonenyl.

A preferred embodiment of the present invention provides a compound represented by general formula (Ia) or (Ib), or stereoisomers, solvates, metabolites, prodrugs, pharmaceutically acceptable salts or cocrystals thereof, wherein $R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, a $C_{1-6}$ alkyl, a $C_{2-6}$ alkenyl, or a $C_{2-6}$ alkynyl, wherein the alkyl, alkenyl, or alkynyl is optionally further substituted with 0 to 6 substituents selected from F, Cl, Br, I, a $C_{1-6}$ alkyl, or a 3- to 6-membered carbocyclyl;

alternatively, any pair of $R^3$ and $R^{3'}$, and $R^9$ and $R^{9'}$ forms

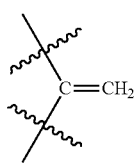

together with the carbon atom to which they are attached;

alternatively, any pair of $R^3$ and $R^{3'}$, and $R^9$ and $R^{9'}$ forms a 3- to 6-membered carbocycle together with the carbon atom to which they are attached;

$R^7$ is selected from H or an amino-protecting group; and $R^8$ is selected from H or a carboxy-protecting group.

A preferred embodiment of the present invention provides a compound represented by general formula (Ia) or (Ib), or stereoisomers, solvates, metabolites, prodrugs, pharmaceutically acceptable salts or cocrystals thereof, wherein $R^{1'}$, $R^2$, $R^3$, $R^{3'}$, $R^{4'}$, $R^5$, $R^{5'}$, $R^6$, $R^9$ or $R^{9'}$ is each independently selected from substituted or unsubstituted H, F, Cl, Br, I, methyl, ethyl, isopropyl, propyl, vinyl, propenyl, ethynyl or propynyl; when substituted, they are substituted with 1 to 6 substituents selected from F, Cl, Br, I, methyl or ethyl;

alternatively, $R^3$ and $R^{3'}$ together with the carbon atom to which they are attached form

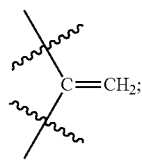 [SMILES: *C(*)=C]

alternatively, $R^3$ and $R^{3'}$ together with the carbon atom to which they are attached form cyclopropyl, cyclobutyl or cyclopentyl; $R^7$ is H; and $R^8$ is H.

In a preferred embodiment of the present invention, the present invention relates to a compound selected from, but not limited to:

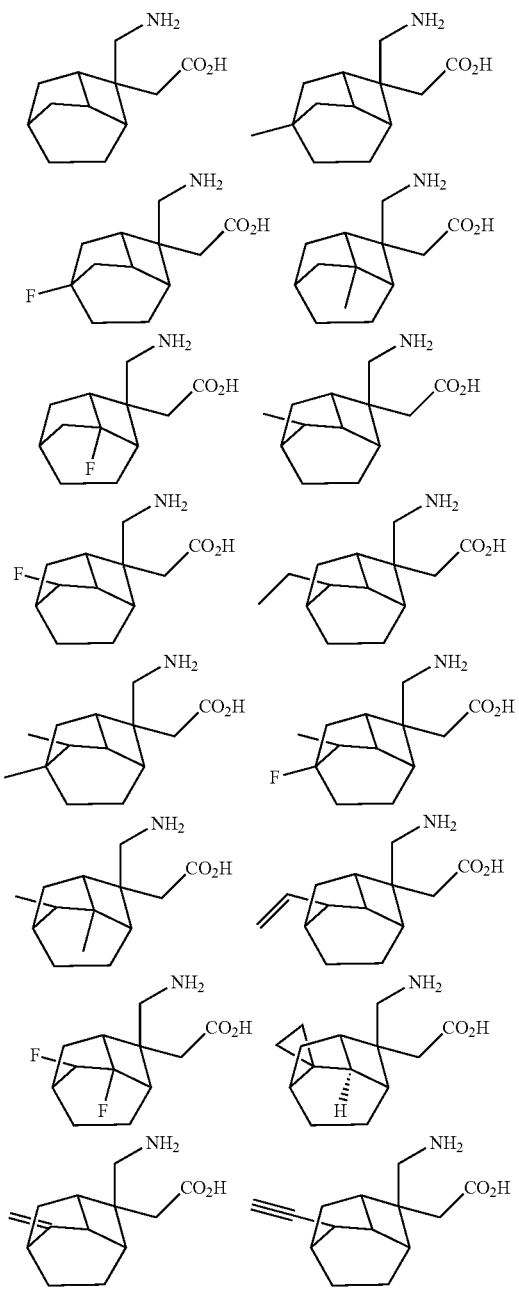

-continued
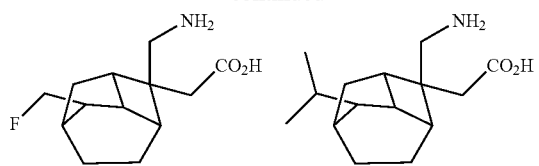
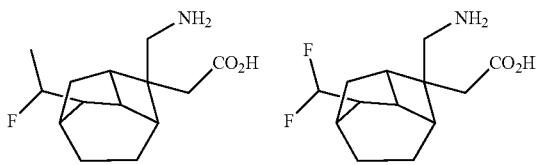
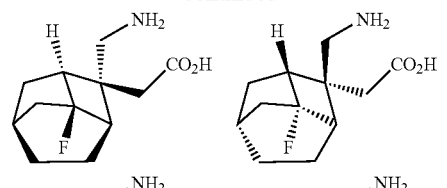
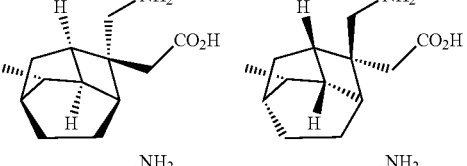
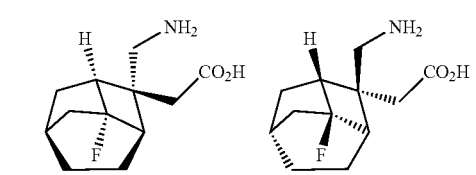

-continued

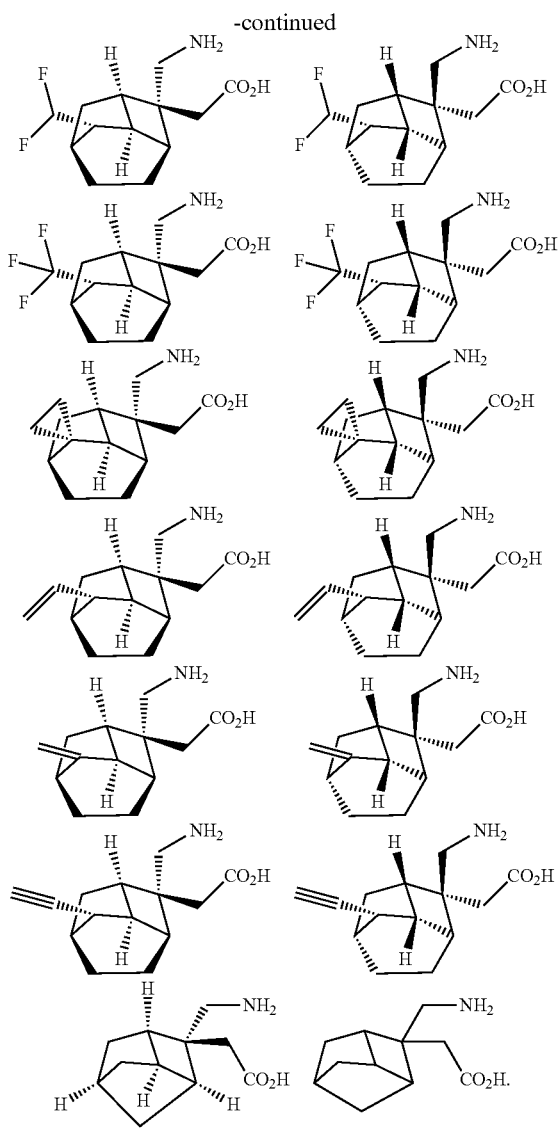

A preferred embodiment of the present invention provides a compound according to the present invention, or stereoisomers, solvates, metabolites, prodrugs, pharmaceutically acceptable salts or cocrystals thereof, wherein the salts are selected from benzenesulfonate, p-toluenesulfonate or mesylate.

An embodiment of the present invention relates to a pharmaceutical composition, comprising a compound represented by general formula (I), (Ia) or (Ib) or all stereoisomers, solvates, metabolites, pharmaceutically acceptable salts, cocrystals, or prodrugs thereof; and one or more pharmaceutically acceptable carriers and/or excipients.

An embodiment of the present invention relates to use of a compound represented by general formula (I), (Ia) or (Ib) or all stereoisomers, solvates, metabolites, pharmaceutically acceptable salts, cocrystals or prodrugs thereof, or a pharmaceutical composition comprising the compound, in the manufacture of a medicament for treating and/or preventing pain.

The use is preferably for treatment of postherpetic neuralgia, trigeminal neuralgia, migraine, pain associated with osteoarthritis or articular rheumatism, lower back pain, sciatica, toothache, pain caused by burns, pain caused by diabetic neuropathy, pain caused by chemotherapy-induced neuropathy, HIV-related neuralgia, AIDS-related neuralgia, cancer-related neuralgia or non-neuralgia pains, acute or chronic tension headache, postoperative pain, fibromyalgia, epilepsy, extensive anxiety or restless leg syndrome.

An embodiment of the present invention relates to an intermediate for preparation of a compound of general formula (I), or a stereoisomer or a pharmaceutically acceptable salt thereof, wherein:

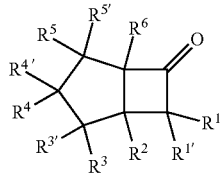

(Z)

$R^1$ and $R^4$ bond each other to form —$(CR^9R^{9'})_n$— or —$CR^9$=$CR^{9'}$—;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, amino, carboxy, carboxylate, amide group, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl, wherein the alkyl, alkoxy, sulfanyl, alkenyl, alkynyl, carbocyclyl or heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl, and the heterocyclyl contains 1 to 2 heteroatoms selected from N, O or S;

n is selected from 1, 2 or 3;

alternatively, any pair of $R^3$ and $R^{3'}$, $R^5$ and $R^{5'}$, and $R^9$ and $R^{9'}$ forms

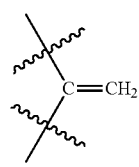

together with the carbon atom to which they are attached, and the

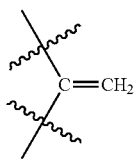

is optionally further substituted with 0 to 2 substituents selected from F, Cl, Br, I, a $C_{1-6}$ alkyl, a 3- to 6-membered carbocyclyl or a 3- to 6-membered heterocyclyl, wherein the alkyl, 3- to 6-membered carbocyclyl or 3- to 6-membered heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl;

alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, amino, a $C_{1-6}$ alkyl, a $C_{1-6}$ alkoxy, or a $C_{1-6}$ sulfanyl.

A preferred embodiment of the present invention provides a compound represented by general formula (Z), or a stereoisomer or a pharmaceutically acceptable salt thereof, wherein the compound is selected from those represented by general formula (Z-1) or (Z-2):

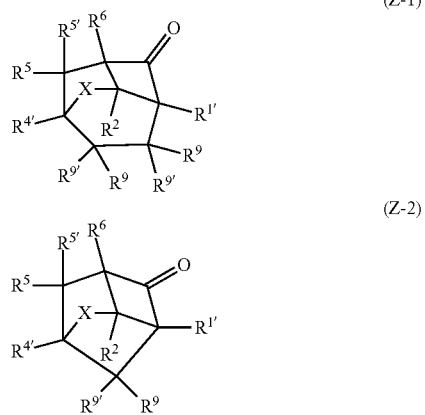

X represents $CR^3R^{3'}$;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, a $C_{1-6}$ alkyl, a $C_{2-6}$ alkenyl, or a $C_{2-6}$ alkynyl, wherein the alkyl, alkenyl, or alkynyl is optionally further substituted with 0 to 6 substituents selected from F, Cl, Br, I, a $C_{1-6}$ alkyl, or a 3- to 6-membered carbocyclyl;

alternatively, any pair of $R^3$ and $R^{3'}$, and $R^9$ and $R^{9'}$ forms

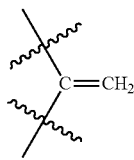

together with the carbon atom to which they are attached;

alternatively, any pair of $R^3$ and $R^{3'}$, and $R^9$ and $R^{9'}$ forms a 3- to 6-membered carbocycle together with the carbon atom to which they are attached.

A preferred embodiment of the present invention provides a compound represented by general formula (Z), or a stereoisomer or a pharmaceutically acceptable salt thereof, wherein:

$R^{1'}$, $R^2$, $R^3$, $R^{3'}$, $R^{4'}$, $R^5$, $R^{5'}$, $R^6$, $R^9$ or $R^{9'}$ is each independently selected from substituted or unsubstituted H, F, Cl, Br, I, methyl, ethyl, isopropyl, propyl, vinyl, propenyl, ethynyl or propynyl; when substituted, they are substituted with 1 to 6 substituents selected from F, Cl, Br, I, methyl or ethyl;

alternatively, $R^3$ and $R^{3'}$ together with the carbon atom to which they are attached form

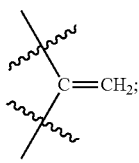 [SMILES: *C(*)=C]

alternatively, $R^3$ and $R^{3'}$ together with the carbon atom to which they are attached form cyclopropyl, cyclobutyl or cyclopentyl.

A preferred embodiment of the present invention provides a compound represented by general formula (Z), or a stereoisomer or a pharmaceutically acceptable salt thereof, wherein the compound is one selected from:

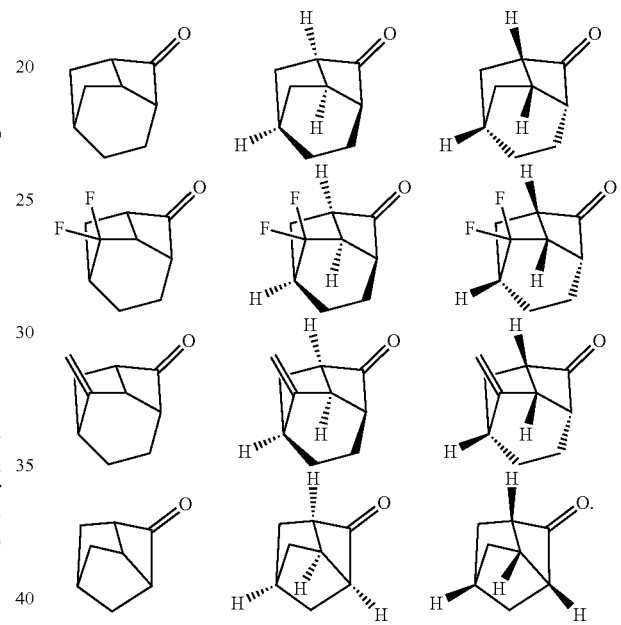

Unless otherwise indicated, the terms used throughout the specification and claims have the following meanings.

All of the carbon, hydrogen, oxygen, sulfur, nitrogen or F, Cl, Br, I involved in the groups and compounds according to the present invention include their isotopes. All of the carbon, hydrogen, oxygen, sulfur or nitrogen involved in the groups and compounds according to the present invention are optionally further replaced by one or more of their corresponding isotopes, wherein the carbon isotopes include $^{12}C$, $^{13}C$ and $^{14}C$, the hydrogen isotopes include protium (H), deuterium (D, also known as heavy hydrogen) and tritium (T, also known as superheavy hydrogen), the oxygen isotopes include $^{16}O$, $^{17}O$ and $^{18}O$, the sulfur isotopes include $^{32}S$, $^{33}S$, $^{34}S$ and $^{36}S$, the nitrogen isotopes include $^{14}N$ and $^{15}N$, the fluorine isotopes include $^{17}F$ and $^{19}F$, the chlorine isotopes include $^{35}Cl$ and $^{37}Cl$, and the bromine isotopes include $^{79}Br$ and $^{81}Br$.

"Alkyl" means a linear or branched saturated aliphatic hydrocarbonyl having 1 to 20 carbon atoms, preferably 1 to 8 carbon atoms, more preferably 1 to 6 carbon atoms, and even more preferably 1 to 4 carbon atoms. Non-limiting examples include methyl, ethyl, n-propyl, isopropyl, n-butyl, sec-butyl, neo-butyl, t-butyl, n-pentyl, isopentyl, neo-pentyl, n-hexyl, and various branched isomers thereof. The alkyl may be optionally further substituted with 0 to 6 substituents selected from F, Cl, Br, I, hydroxyl, thiol, nitro, cyano, amino, alkylamino, amide group, alkenyl, alkynyl, a $C_{1-6}$ alkyl, a $C_{1-6}$ hydroxyalkyl, a $C_{1-6}$ alkoxy, a 3- to 8-membered carbocyclyl, a 3- to 8-membered heterocyclyl, a 3- to 8-membered carbocyclyloxy, a 3- to 8-membered heterocyclyloxy, carboxy, or carboxylate. Alkyl used in the present disclosure has the meaning defined herein.

"Alkoxy" means a —O-alkyl. Non-limiting examples include methoxy, ethoxy, n-propoxy, isopropoxy, n-butoxy, sec-butoxy, t-butoxy, n-pentyloxy or n-hexyloxy. The alkyl may be optionally further substituted with 0 to 5 substituents selected from F, Cl, Br, I, hydroxyl, thiol, nitro, cyano, amino, alkylamino, alkenyl, alkynyl, alkyl, hydroxyalkyl, alkoxy, carbocyclyl, heterocyclyl, carbocyclyloxy, heterocyclyloxy, carboxy or carboxylate. Alkoxy used in the present disclosure has the meaning defined herein.

"Sulfanyl" refers to a S-alkyl. Non-limiting examples include methylthio, ethylthio, n-propylthio, isopropylthio, n-butylthio, sec-butylthio, t-butylthio, n-pentylthio or n-hexylthio. The alkyl may be optionally further substituted with 0 to 5 substituents selected from F, Cl, Br, I, hydroxyl, thiol, nitro, cyano, amino, alkylamino, alkenyl, alkynyl, alkyl, hydroxyalkyl, alkoxy, carbocyclyl, heterocyclyl, carbocyclyloxy, heterocyclyloxy, carboxy or carboxylate. Sulfanyl used in the present disclosure has the meaning defined herein.

"Amino" refers to —$NH_2$.

"Cyano" refers to

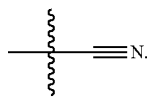

"Hydroxyl" refers to —OH.

"Thiol" refers to —SH.

"Carboxy" refers to —COOH.

"Carboxylate" refers to —$COOR^{10}$, wherein $R^{10}$ is a $C_{1-6}$ alkyl.

"Amide group" refers to —$CONR^{11}R^{11'}$, wherein $R^{11}$ and $R^{11'}$ are each independently selected from H, alkyl or carbocyclyl, and $R^{11}$ and $R^{11'}$ may optionally be further substituted with 0 to 3 substituents selected from F, Cl, Br, I, hydroxyl, thiol, —$SR^{12}$, nitro, cyano, amino, alkylamino, amide group, alkenyl, alkynyl, alkyl, hydroxyalkyl, alkoxy, carbocyclyl, heterocyclyl, carbocyclyloxy, heterocyclyloxy, carboxy or carboxylate, wherein $R^{12}$ is selected from a $C_{1-6}$ alkyl, a 3- to 8-membered carbocyclyl or a 3- to 8-membered heterocyclyl.

"Alkenyl" refers to a linear or branched unsaturated aliphatic hydrocarbonyl having 1 to 3 carbon-carbon double bonds, and consisting of 2 to 20 carbon atoms, preferably 2 to 12 carbon atoms, more preferably 2 to 8 carbon atoms, and even more preferably 2 to 6 carbon atoms. Non-limiting examples include vinyl, propen-2-yl, buten-2-yl, buten-3-yl, penten-2-yl, penten-4-yl, hexen-2-yl, hexene-3-yl, hepten-2-yl, hepten-3-yl, hepten-4-yl, octen-3-yl, nonen-3-yl, decen-4-yl and undecen-3-yl. The alkenyl may be optionally further substituted with 0 to 6 substituents selected from F, Cl, Br, I, alkyl, alkoxy, linear alkenyl, linear alkynyl, amino, nitro, cyano, thiol, amide group, carbocyclyl or heterocyclyl.

"Alkynyl" refers to a linear or branched unsaturated aliphatic hydrocarbonyl having 1 to 3 carbon-carbon triple bonds, and consisting of 2 to 20 carbon atoms, preferably 2 to 12 carbon atoms, more preferably 2 to 8 carbon atoms, and even more preferably 2 to 6 carbon atoms. Non-limiting examples include ethynyl, propyn-1-yl, propyn-2-yl, butyn-1-yl, butyn-2-yl, butyn-3-yl, 3,3-dimethylbutyn-2-yl, pentyn-1-yl, pentyn-2-yl, hexyn-1-yl, 1-heptyn-1-yl, heptyn-3-yl, heptyn-4-yl, octyn-3-yl, nonyn-3-yl, decyn-4-yl, undecyn-3-yl, and dodecyn-4-yl. The alkynyl may be optionally further substituted with 0 to 4 substituents selected from F, Cl, Br, I, alkyl, alkoxy, linear alkenyl, linear alkynyl, amino, nitro, cyano, thiol, amide group, carbocyclyl or heterocyclyl.

"Carbocyclyl" refers to a saturated or unsaturated non-aromatic cyclic group which may be a 3- to 8-membered monocyclic ring, a 4- to 12-membered fused ring, or a 10- to 15-membered tricyclic ring system, and may be attached with a bridged or spiro ring. Non-limiting examples include cyclopropyl, cyclobutyl, cyclopentyl, cyclohexyl, cycloheptyl, cyclooctyl, cyclodecyl, cyclododecyl, cyclobutenyl, cyclopentenyl, cyclohexenyl,

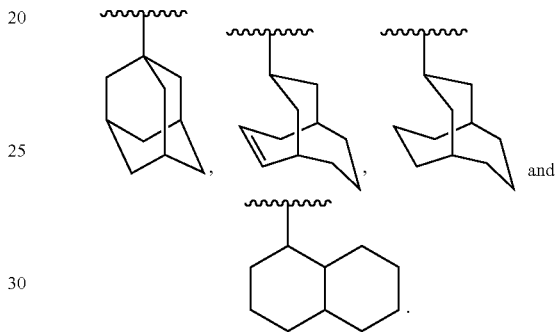

The carbocyclyl may be optionally further substituted with 0 to 8 substituents selected from F, Cl, Br, I, =O, hydroxyl, thiol, nitro, cyano, amino, alkylamino, amide, alkenyl, alkynyl, alkyl, hydroxyalkyl, alkoxy, carbocyclyl, heterocyclyl, carbocyclyloxy, heterocyclyloxy, carboxy or carboxylate. Carbocyclyl used in the present disclosure has the meaning defined herein.

"Heterocyclyl" refers to a substituted or unsubstituted, saturated or unsaturated, aromatic or non-aromatic ring having 1 to 3 heteroatoms selected from N, O or S, and the aromatic or non-aromatic ring may be a 3- to 8-membered monocyclic ring, a 4- to 12-membered bicyclic ring, or a 10- to 15-membered tricyclic ring system. The N and S optionally substituted in the ring of a heterocyclyl may be oxidized to various oxidative states. A heterocyclyl may be attached to a heteroatom or a carbon atom, and may be attached with a bridged or spiro ring. Non-limiting examples include epoxyethyl, aziridinyl, oxetanyl, azetidinyl, 1,3-dioxolanyl, 1,4-dioxolanyl, 1,3-dioxane, azepanyl, pyridyl, furyl, thienyl, pyranyl, N-alkylpyrrolyl, pyrimidinyl, pyrazinyl, pyridazinyl, imidazolyl, piperidinyl, morpholinyl, thiomorpholinyl, 1,3-dithianyl, dihydrofuryl, dihydropyranyl, dithiolanyl, tetrahydrofuranyl, tetrahydropyrrolyl, tetrahydroimidazolyl, tetrahydrothiazolyl, tetrahydropyranyl, benzimidazolyl, benzopyridyl, pyrrolopyridyl, benzodihydrofuranyl, azabicyclo[3.2.1]octanyl, azabicyclo[5.2.0]nonanyl, oxatricyclo[5.3.1.1]dodecanyl, azadamantyl, and oxaspiro[3.3]heptyl. The heterocyclyl may be optionally further substituted with 0 to 5 substituents selected from F, Cl, Br, I, =O, hydroxyl, thiol, nitro, cyano, amino, alkylamino, amide group, alkenyl, alkynyl, alkyl, hydroxyalkyl, alkoxy, carbocyclyl, heterocyclyl, carbocyclyloxy, heterocyclyloxy, carboxy or carboxylate. Heterocyclyl used in the present disclosure has the meaning defined herein.

An "amino-protecting group" refers to a group for protecting amino, which is suitable for protecting an amino group from a chemical reaction but is easily removed after a desired chemical reaction is completed at other parts of the molecule. Non-limiting examples include but are not limited to formyl, acetyl, phenylacyl, methoxycarbonyl, ethoxy carbonyl, 2,2,2-trichloroethoxycarbonyl, propoxycarbonyl, t-butoxycarbonyl, benzyloxycarbonyl, phenoxycarbonyl, 9-fluorenylmethoxycarbonyl, adamantyloxycarbonyl, benzyloxycarbonyl, benzylcarbonyl, benzyl, phenylmethyl, trityl, and phthaloyl.

A "carboxy-protecting group" refers to a group for protecting carboxy, which is suitable for protecting a carboxy group from a chemical reaction but is easily removed after a desired chemical reaction is completed at other parts of the molecule. Non-limiting examples include but are not limited to methyl, ethyl, n-propyl, isopropyl, n-butyl, sec-butyl, neobutyl, t-butyl, n-pentyl, isopentyl, neopentyl, n-hexyl, trichloroethyl, benzyl, p-nitrobenzyl, o-nitrobenzyl, p-methoxybenzyl, p-t-butylbenzyl, acetoxymethyl, propionyloxymethyl, butyryloxymethyl, isobutyryloxymethyl, pentoxymethyl, pivaloyloxymethyl, acetoxyethyl, acetoxypropyl, acetoxybutyl, propionyloxyethyl, propionyloxypropyl, butyryloxyethyl, isobutyryloxyethyl, pivaloyloxyethyl, hexanoyloxyethyl, isobutyryloxymethyl, ethylbutyryloxymethyl, dimethylbutyryloxymethyl, pentanoyloxyethyl, methoxycarbonyloxymethyl, ethoxycarbonyloxymethyl, propoxycarbonyloxyethyl, isopropoxycarbonyloxyethyl, t-butoxycarbonyloxymethyl, methoxycarbonyloxyethyl, ethoxycarbonyloxyethyl, isopropoxycarbonyloxyethyl, t-butyl(dimethyl)silyl, trimethylsilyl, methoxymethyl, ethoxymethyl, propoxymethyl, isopropoxymethyl, (2-methylthio)ethyl, 3-methyl-2-butenyl, 5-indanyl and 3-2-benzo[C]furanonenyl.

A "pharmaceutically acceptable salt" or "pharmaceutically acceptable salt thereof" refers to a salt of the compound according to the present invention that retains the biological effectiveness and characteristics of the free acid or free base form, and is obtained by a reaction between the free acid with a non-toxic inorganic or organic base, or between the free base with a non-toxic inorganic or organic acid.

A "pharmaceutical composition" refers to a mixture of one or more of the compounds according to the present invention or a pharmaceutically acceptable salt or a prodrug thereof with other chemical components, wherein the "other chemical components" refer to pharmaceutically acceptable carriers or excipients and/or one or more additional therapeutic agents.

"Carrier" means a material that does not cause significant stimulation to an organism and does not eliminate the biological activity and characteristics of a given compound.

"Excipient" means an inert substance added into a pharmaceutical composition to facilitate administration of a compound. Non-limiting examples include calcium carbonate, calcium phosphate, sugars, starch, cellulose derivatives (including microcrystalline cellulose), gelatin, vegetable oils, polyethylene glycols, diluent, a granulating agent, lubricant, binder, and disintegrant.

A "prodrug" means a compound that can be converted by in vivo metabolism into the biologically active compound according to the present invention. A prodrug according to the present invention is prepared by modification of an amino or carboxy in the compound according to the present invention. Such a modification can be removed in vivo or by conventional operations, so as to produce the parent compound. When a prodrug according to the present invention is administered to a mammal individual, it is cleaved to form free amino or carboxy group(s).

A "cocrystal" refers to a crystal formed by bonding an active pharmaceutical ingredient (API) and a cocrystal former (CCF) through an action of hydrogen bonds or other non-covalent bonds, wherein both API and CCF in their pure form are solid at room temperature and these components are present in a fixed stoichiometric ratio therebetween. A cocrystal is a multi-component crystal, encompassing both a binary cocrystal formed by two neutral solids and a multiple cocrystal formed by neutral solids and a salt or solvate.

An "animal" includes mammals, such as humans, companion animals, zoo animals, and domestic animals, preferably humans, horses, or dogs.

A "stereoisomer" refers to an isomer due to a different spatial arrangement of atoms in a molecule, including cis-trans isomers, enantiomers, and conformational isomers.

"Optional" or "optionally" means that the event or scenario described by it may, but does not have to, happen, and encompasses both cases where the event or scenario happens and does not happen. For example, "a heterocyclyl optionally substituted with an alkyl" means that the alkyl may, but does not have to, be present, encompassing both the case where the heterocyclyl is substituted with an alkyl and the case where the heterocyclyl is not substituted with an alkyl.

"$IC_{50}$" (half maximal inhibitory concentration of the inhibitor measured): the concentration of a test compound required to inhibit 50% of the binding of gabapentin to a calcium channel.

DESCRIPTION OF DRAWINGS

The FIGURE shows the experimental results in a L5-L6 spinal nerve ligation (SNL) animal model.

DETAILED DESCRIPTION OF INVENTION

The technical solutions of the present invention are described in detail hereinafter in connection with the FIGURE and Examples, but the scope of protection of the present invention is not limited thereto.

The structures of compounds were determined by nuclear magnetic resonance (NMR) and/or mass spectroscopy (MS). NMR shifts (δ) are presented in $10^{-6}$ ppm. NMR measurements were performed with a Bruker ADVANCE III 400 NMR device and a Brucker ADVANCE 300 NMR device, wherein the measurement solvents were hexadeuterodimethyl sulfoxide (DMSO-$d_6$), deuterochloroform (CDCl$_3$), and deuteromethanol (CD$_3$OD), and the internal reference was tetramethylsilane (TMS).

MS measurements were performed with Agilent 6120B (ESI) and Agilent 6120B (APCI).

HPLC measurements were performed with Agilent 1260DAD High-pressure Liquid Chromatograph (Zorbax SB-C18 100×4.6 mm, 3.5 μM).

Thin-layer chromatography silica gel plate: HSGF254 silica gel plate (Huanghai, Yantai) or GF254 silica gel plate (Qingdao). The specification of the silica gel plate used for thin-layer chromatography (TLC) was 0.15 mm to 0.20 mm, and that for product isolation and purification by TLC was 0.4 mm to 0.5 mm.

The column chromatography generally used the silica gel (Huanghai, Yantai) of 200 to 300 mesh as a carrier.

Known starting materials in the present invention can be synthesized following or using methods known in the art, or can be purchased from companies such as Titansci, Energy Chemical, Demochem (Shanghai), Kelong Chemical (Chengdu), Accela ChemBio, and J&K Scientific.

A $N_2$ atmosphere means that the reaction vessel is connected to a $N_2$ balloon of about 1 L in volume.

A $H_2$ atmosphere means that the reaction vessel is connected to a $H_2$ balloon of about 1 L in volume.

Hydrogenation reactions generally involve a vacuuming and Hz-charging operation repeated 3 times.

In the Example, unless particularly specified, reactions were carried out under a $N_2$ atmosphere.

In the Example, unless particularly specified, solutions refer to aqueous solutions.

In the Example, unless particularly specified, reaction temperatures are room temperature, and most suitable room temperature as a reaction temperature is 20° C. to 30° C.

Et means ethyl.

$^tBu$ means t-butyl.

Intermediate 1

(±)-t-butyl 2-((1R,2R,3S,6R,8R)-2-(nitromethyl)tricyclo[4.2.1.0$^{3,8}$]nonan-2-yl)acetate

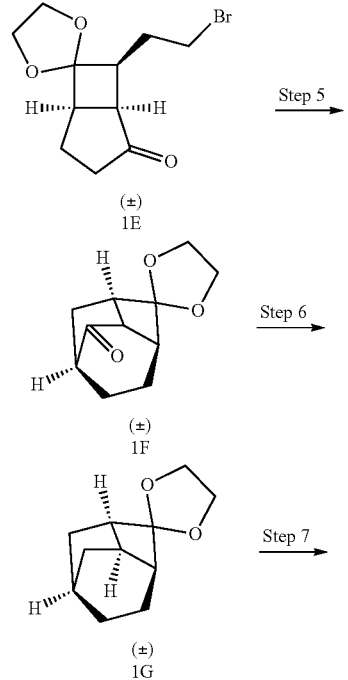

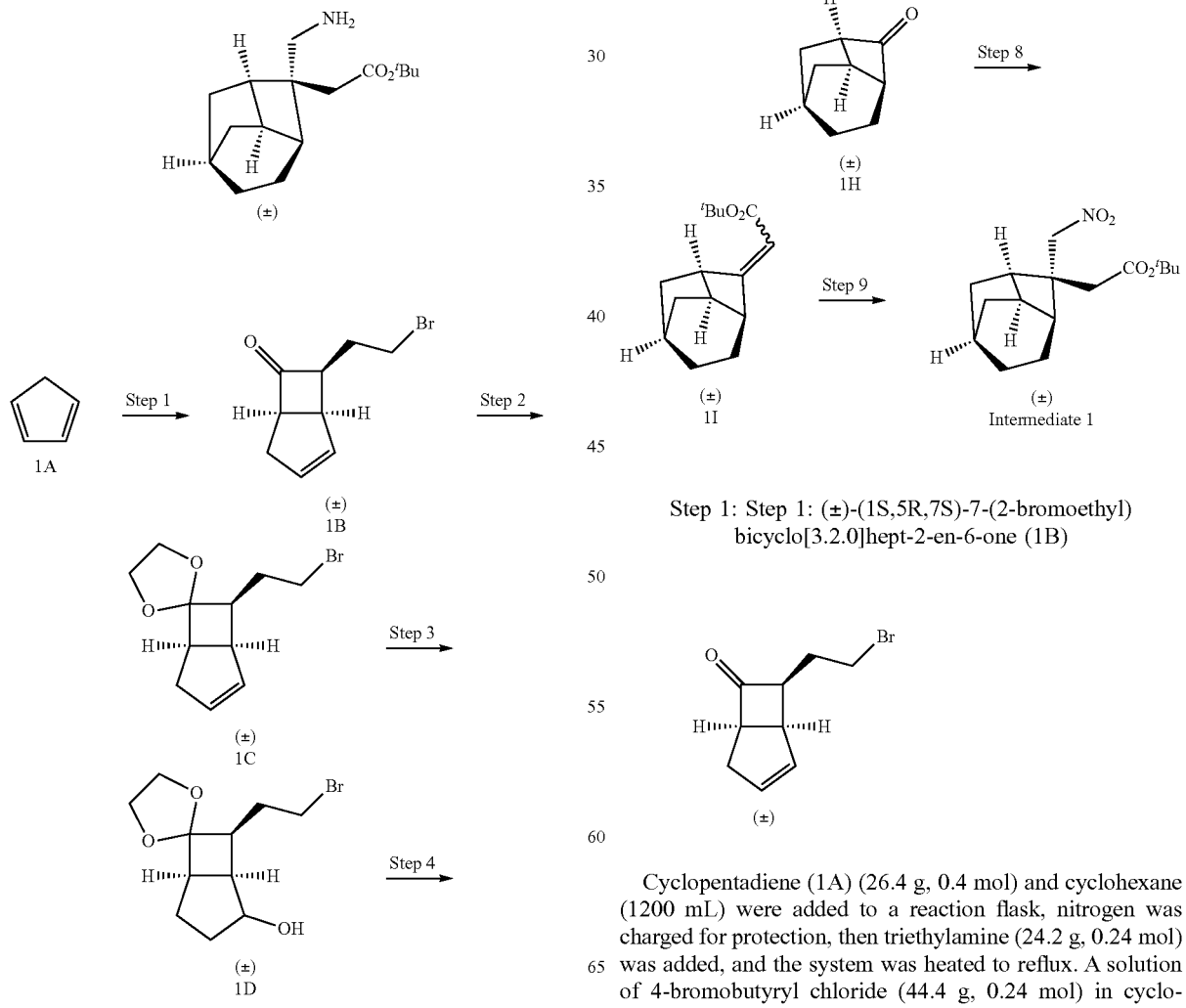

Step 1: Step 1: (±)-(1S,5R,7S)-7-(2-bromoethyl)bicyclo[3.2.0]hept-2-en-6-one (1B)

Cyclopentadiene (1A) (26.4 g, 0.4 mol) and cyclohexane (1200 mL) were added to a reaction flask, nitrogen was charged for protection, then triethylamine (24.2 g, 0.24 mol) was added, and the system was heated to reflux. A solution of 4-bromobutyryl chloride (44.4 g, 0.24 mol) in cyclohexane was added dropwise (50 mL, 25 mL/h), followed by a reaction at reflux for 4 hours. After cooling to room temperature, the reaction solution was filtered by suction, and washed with cyclohexane (100 mL×3). The filtrates were combined and washed sequentially with saturated ammonium chloride (500 mL×3) and water (500 mL×3), dried over anhydrous sodium sulfate, and filtered. The filtrate was concentrated under reduced pressure. The residue was purified by silica gel column chromatography (petroleum ether/ethyl acetate (v/v)=80:1) to obtain (±)-(1S, 5R,7S)-7-(2-bromoethyl)bicyclo[3.2.0]hept-2-en-6-one (1B) (12 g, yield: 24%) as a light yellow oil.

$^1$H NMR (400 MHz, CDCl$_3$) δ 5.97-5.85 (m, 1H), 5.80-5.70 (m, 1H), 3.91-3.79 (m, 1H), 3.67 (dd, 2H), 3.47 (t, 2H), 2.68 (ddd, 1H), 2.47-2.31 (m, 1H), 2.13 (dq, 1H), 1.93 (ddd, 1H).

Step 2: (±)-(1S,5R,7S)-7-(2-bromoethyl)spiro[bicyclo[3.2.0]hept[2]ene-6,2'-[1,3]dioxolane] (1C)

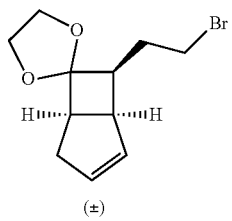 [SMILES: BrCC[C@H]1[C@H]2C=CC[C@H]2C12OCCO2]

(±)

(±)-(1S,5R,7S)-7-(2-bromoethyl)bicyclo[3.2.0]hept-2-en-6-one (1B) (37 g, 0.173 mol), p-toluenesulfonic acid monohydrate (1.6 g, 8.6 mmol), ethylene glycol (42.9 g, 0.692 mol) and toluene (320 mL) were sequentially added to a reaction flask, and heated to reflux, and water was distilled off for 5 hours. After cooling, the reaction solution was poured into ice water, to which a saturated solution of sodium bicarbonate was added until the pH reached about 7. The mixture was extracted with ethyl acetate (400 ml×3). The organic phases were combined, dried over anhydrous sodium sulfate, and filtered. The filtrate was concentrated under reduced pressure. The residue was purified by silica gel column chromatography (petroleum ether/ethyl acetate (v/v)=100:1), to obtain (±)-(1S,5R,7S)-7-(2-bromoethyl) spiro[bicyclo[3.2.0]hept[2]ene-6,2'-[1,3]dioxolane] (1C) (27.4 g, yield: 61%) as a yellow oil.

$^1$H NMR (400 MHz, CDCl$_3$) δ 5.94-5.83 (m, 1H), 5.67-5.56 (m, 1H), 3.95-3.75 (m, 4H), 3.36-3.25 (m, 2H), 3.23-3.12 (m, 1H), 3.02 (ddd, 2H), 2.48-2.25 (m, 2H), 1.99-1.78 (m, 2H).

Step 3: (±)-(1S,5R,7S)-7-(2-bromoethyl)spiro[bicyclo[3.2.0]heptane-6,2'-[1,3]dioxolan]-2-ol (1D)

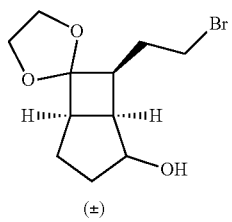 [SMILES: OC1CC[C@@H]2[C@H]1[C@H](CCBr)C21OCCO1]

(±)

(±)-(1S,5R,7S)-7-(2-bromoethyl)spiro[bicyclo[3.2.0]hept[2]ene-6,2'-[1,3]dioxolane] (1C) (27.4 g, 0.11 mol) and tetrahydrofuran (330 mL) were added to a reaction flask, a borane dimethyl sulfide solution (55 mL, 0.55 mol) was added dropwise in an ice water bath, and a reaction was carried out for 2 hours in the ice water bath. Then purified water (1.1 mol), an aqueous solution of sodium hydroxide (3 mol/L, 360 mL) and hydrogen peroxide solution (containing 1.1 mol H$_2$O$_2$) were sequentially added dropwise, and then the mixture was warmed to room temperature to react for 3 hours. The mixture was extracted with ethyl acetate (500 mL×3), and the organic phase was washed with a saturated solution of sodium bicarbonate (500 mL×2) and with water (500 mL×2), dried over anhydrous sodium sulfate, and filtered. The filtrate was concentrated under reduced pressure, to obtain (±)-(1S,5R,7 S)-7-(2-bromoethyl)spiro[bicyclo[3.2.0]heptane-6,2'-[1,3]dioxolan]-2-ol (1D) (30 g) as a light yellow oily liquid, which was directly used for the next step.

Step 4: (±)-(1S,5R,7 S)-7-(2-bromoethyl)spiro[bicyclo[3.2.0]heptane-6,2'-[1,3]dioxolan]-2-one (1E)

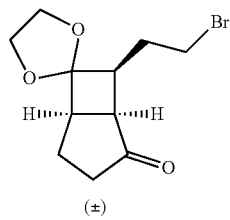 [SMILES: O=C1CC[C@@H]2[C@H]1[C@H](CCBr)C21OCCO1]

(±)

(±)-(1S,5R,7 S)-7-(2-bromoethyl)spiro[bicyclo[3.2.0] heptane-6,2'-[1,3]dioxolan]-2-ol (1D) (30 g, 0.11 mol) and dichloromethane (500 mL) were added to a reaction flask, and Dess-Martin periodinane (70 g, 0.17 mol) was added in batches while in an ice bath, followed by a reaction at room temperature for 2 hours. Dichloromethane (300 mL) and an aqueous solution of sodium thiosulfate (2 mol/L, 500 mL) were added to the reaction mixture, followed by stirring for 30 minutes to allow partitioning. The aqueous phase was extracted with dichloromethane (300 mL×2). The organic phases were combined and washed with a solution of sodium hydroxide (2 mol/L, 500 mL×2) and water (500 mL×2), dried over anhydrous sodium sulfate, and filtered. The filtrate was concentrated under reduced pressure. The residue was purified by silica gel column chromatography (petroleum ether/ethyl acetate (v/v)=10:1) to obtain (±)-(1S, 5R,7 S)-7-(2-bromoethyl)spiro[bicyclo[3.2.0]heptane-6,2'-[1,3]dioxolan]-2-on e (1E) (15 g, yield: 50%) as a light yellow oily liquid.

$^1$H NMR (400 MHz, CDCl$_3$) δ 4.02-3.81 (m, 4H), 3.40 (dd, J=10.3, 3.8 Hz, 2H), 3.15 (td, J=10.3, 4.9 Hz, 2H), 2.61 (ddd, J=20.6, 14.0, 8.1 Hz, 2H), 2.27 (ddt, J=18.9, 9.6, 1.8 Hz, 1H), 2.12-2.00 (m, 1H), 1.99-1.70 (m, 3H).

Step 5: (±)-(1'R,3'S,6'S,8'R)-spiro[[1,3]dioxolane-2, 2'-tricyclo[4.2.1.0³,⁸]nonan]-7'-one (1F)

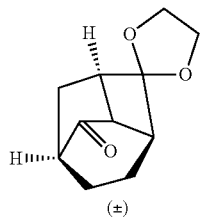 [SMILES: O=C1C2[C@H]3C[C@@H]1CC[C@@H]2C31OCCO1]

(±)

Potassium t-butoxide (0.58 g, 5.2 mmol) and toluene (40 mL) were added to a reaction flask, nitrogen was charged for protection, and the mixture was cooled to −15° C. A solution of (±)-(1S,5R,7 S)-7-(2-bromoethyl)spiro[bicyclo[3.2.0] heptane-6,2'-[1,3]dioxolan]-2-one (1E) in toluene (1.1 g, 1 mmol, 5 mL) was added dropwise, and the mixture was allowed to react at −15° C. for 1 hour and then warmed to 0° C., followed by stirring for 1 hour. While in an ice bath, a saturated solution of ammonium chloride was added dropwise until the pH reached about 7. The mixture was extracted with ethyl acetate (80 ml×3). The organic phase was washed with water (80 ml×2), dried over anhydrous sodium sulfate, and filtered. The filtrate was concentrated under reduced pressure. The residue was purified by silica gel column chromatography (petroleum ether/ethyl acetate (v/v)=8:1), to obtain (±)-(1'R,3'S,6'S,8'R)-spiro[[1,3]dioxolane-2,2'-tricyclo[4.2.1.0³,⁸]nonan]-7'-one (1F) (0.4 g, yield 51%) as a light yellow oil.

$^1$H NMR (400 MHz, CDCl$_3$) δ 4.04-3.86 (m, 4H), 3.20-3.07 (m, 1H), 2.99-2.86 (m, 1H), 2.53 (ddd, J=8.6, 5.6, 1.7 Hz, 1H), 2.41-2.24 (m, 2H), 2.24-2.01 (m, 2H), 1.95 (d, J=13.2 Hz, 1H), 1.61 (dddd, J=14.4, 7.6, 2.6, 0.7 Hz, 1H), 1.51-1.38 (m, 1H).

Step 6: (±)-(1'R,3'S,6'R,8'R)-spiro[[1,3]dioxolane-2, 2'-tricyclo[4.2.1.0³,⁸]nonane] (1G)

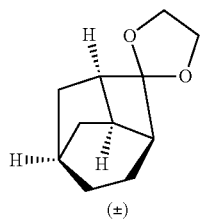 [SMILES: C1COC2(O1)[C@@H]1C[C@@H]3CC[C@H]2[C@H]1C3]

(±)

(±)-(1'R,3'S,6'S,8'R)-spiro[[1,3]dioxolane-2,2'-tricyclo [4.2.1.0³,⁸]nonan]-7'-one (1F) (9.5 g, 49 mmol), diethylene glycol (170 mL), hydrazine hydrate (18.4 g, 294 mmol) and potassium hydroxide (16.5 g, 294 mmol) were added to a reaction flask, followed by a reaction at 180° C. for 3 hours. Water was removed at 70° C. by rotary evaporation under reduced pressure, and the temperature was raised to 220° C., followed by stirring for 2 hours. After cooling to room temperature, water (200 mL) was added to the reaction solution, which was extracted with methyl t-butyl ether (300 mL×3). The organic phase was washed with hydrochloric acid (1 mol/L, 500 mL×2) and water (500 mL×2), dried over anhydrous sodium sulfate, and filtered. The filtrate was concentrated under reduced pressure. The residue was purified by silica gel column chromatography (petroleum ether/ ethyl acetate (v/v)=60:1), to obtain (±)-(1'R,3'S,6'R,8'R)-spiro[[1,3]dioxolane-2,2'-tricyclo[4.2.1.0³,⁸]nonane] (1G) (5.6 g) as a colorless oil, which was directly used for the next step without purification.

Step 7: (±)-(1R,3S,6R,8R)-tricyclo[4.2.1.0³,⁸]nonan-2-one (1H)

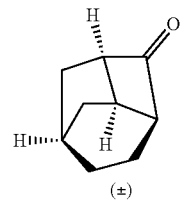

(±)

(±)-(1'R,3'S,6'R,8'R)-spiro[[1,3]dioxolane-2,2'-tricyclo [4.2.1.0³,⁸]nonane] (1G) (5.6 g, 31 mmol), solvent tetrahydrofuran (60 mL) and water (20 mL) were added to a reaction flask, and trifluoroacetic acid (7 g, 62 mmol) was added dropwise while in an ice bath, followed by a reaction at 45° C. for 3 hours. While in an ice bath, a saturated solution of sodium bicarbonate was added dropwise until the pH reached about 7. The mixture was extracted with ethyl acetate (100 ml×3). The organic phase was washed with water (200 ml×2), dried over anhydrous sodium sulfate, and filtered. The filtrate was concentrated under reduced pressure. The residue was purified by silica gel column chromatography (petroleum ether/ethyl acetate (v/v)=100:1), to obtain (±)-(1R,3S,6R,8R)-tricyclo[4.2.1.0³,⁸]nonan-2-one (1H) (3.5 g, yield 83%) as a white solid.

$^1$H NMR (400 MHz, CDCl$_3$) δ 3.47-3.33 (m, 1H), 3.19 (dd, 1H), 2.84-2.69 (m, 1H), 2.47-2.32 (m, 1H), 2.12-1.97 (m, 1H), 1.93 (d, 1H), 1.82-1.69 (m, 1H), 1.56-1.35 (m, 4H), 1.27-1.10 (m, 1H).

Step 8: (±)-tert-butyl 2-41R,3S,6R,8R)-tricyclo [4.2.1.0³,⁸]nonan-2-ylidene)acetate (1I)

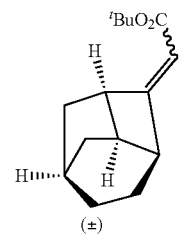 [SMILES: CC(C)(C)OC(=O)C=C1[C@H]2CC[C@@H]3C[C@H]2[C@H]1C3]

(±)

Sodium hydride (60%, 0.8 g, 33.4 mmol) and tetrahydrofuran (80 mL) were added to a reaction flask, and cooled to 0° C. A solution of t-butyl diehylphosphonoacetate (7.5 g, 33.4 mmol) in tetrahydrofuran (10 mL) was added dropwise, followed by a reaction at 0° C. for 20 min. A solution of (±)-(1R,3S,6R,8R)-tricyclo[4.2.1.0³,⁸]nonan-2-one (1H) (3.5 g, 25.7 mmol) in tetrahydrofuran (10 mL) was added dropwise, followed by a reaction at room temperature for 2 hours. Water (100 mL) and ethyl acetate (100 mL) were added to the reaction solution, which was stirred and allowed to partition. The aqueous phase was extracted with ethyl acetate (100 ml×2). The organic phase was dried over anhydrous sodium sulfate and filtered. The filtrate was concentrated under reduced pressure to obtain (±)-tert-butyl 2-41R,3S,6R,8R)-tricyclo[4.2.1.0³,⁸]nonan-2-ylidene)acetate (1I) (5.1 g) as a light yellow oily crude product, which was directly used for the next step.

Step 9: (±)-tert-butyl 2-41R,2R,3S,6R,8R)-2-(nitromethyl)tricyclo[4.2.1.03,8]nonan-2-yl)acetate (Intermediate 1)

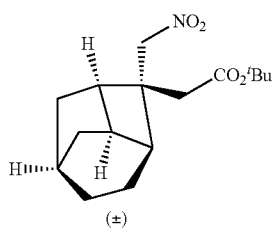

(±)

The crude product obtained in the previous step (±)-tert-butyl 2-41R,3S,6R,8R)-tricyclo[4.2.1.0³,⁸]nonan-2-ylidene)acetate (1I) (5 g, 24.3 mmol), nitromethane (90 mL) and 1,8-diazabicyclo[5.4.0]undec-7-ene (6.6 g, 43.7 mmol) were sequentially added to a reaction flask, and heated to 70° C. to carry out a reaction for 6 hours. Ethyl acetate (100 mL) and a 1 mol/L HCl solution (100 ml) were added to the reaction solution, which was stirred and allowed to partition. The aqueous phase was extracted with ethyl acetate (100 ml×2). The organic phase was dried over anhydrous sodium sulfate and filtered. The filtrate was concentrated under reduced pressure. The residue was purified by silica gel column chromatography (petroleum ether/ethyl acetate (v/v)= 100:1), to obtain (±)-tert-butyl 2-((1R,2R,3S,6R,8R)-2-(nitromethyl)tricyclo[4.2.1.0³,⁸]nonan-2-yl)acetate (Intermediate 1) (5 g, yield 70%) as a colorless oily liquid.

Preparation of Intermediates 2 and 3

Intermediate 2 t-butyl 2-((1R,2R,3S,6R,8R)-2-(nitromethyl)tricyclo[4.2.1.0³,⁸]nonan-2-yl)acetate Intermediate 3 t-butyl 2-((1S,2S,3R,6S,8S)-2-(nitromethyl)tricyclo[4.2.1.0³,⁸]nonan-2-yl)acetate

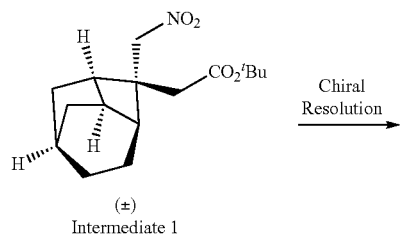

(±)
Intermediate 1

Chiral Resolution →

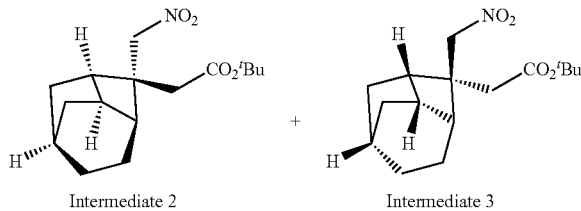

Intermediate 2 + Intermediate 3

(±)-t-butyl 2-((1R,2R,3S,6R,8R)-2-(nitromethyl)tricyclo[4.2.1.0³,⁸]nonan-2-yl)acetate (Intermediate 1) (2 g) was used for chiral resolution. Preparation conditions: Instrument: Thar 350 preparative SFC (SFC-9), column: ChiralPak AD (300×50 mm ID, 10 pin); mobile phase: A: CO₂ B: Methanol; gradient: B 25%; flow rate: 200 mL/min; column temperature: 38° C.

Two optical isomers were obtained after the separation: Peak 1 (retention time: 2.3 minutes, 0.624 g), and Peak 2 (retention time: 3.1 minutes, 0.636 g), wherein Peak 1 was Intermediate 3 (colorless oily liquid, 0.624 g), and Peak 2 was Intermediate 2 (colorless oily liquid, 0.636 g).

Intermediate 4

Ethyl 2-((1R,2R,3S,6S,8R)-7,7-difluoro-2-(nitromethyl)tricyclo[4.2.1.0³,⁸]nonan-2-yl)acetate (+/−) (Intermediate 4)

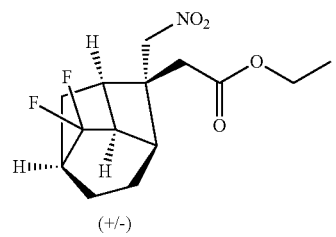 [SMILES: CCOC(=O)C[C@]1(C[N+](=O)[O-])[C@@H]2C[C@@H]3CC[C@H]1[C@H]2C3(F)F]

(+/-)

1F (+/-) → Step 1 → 4b (+/-) → Step 2 → 4c (+/-) → Step 3 →

-continued

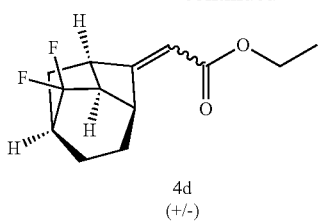

4d
(+/−)

Step 4

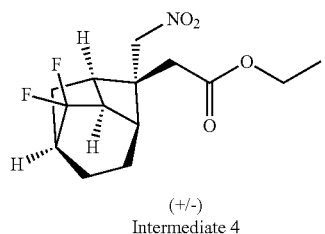

(+/−)
Intermediate 4

Step 1

(1R,3S,6S,8R)-7,7-difluorospiro[tricyclo[4.2.1.0$^{3,8}$]
nonane-2,2'-[1,3]dioxolane](+/−) (4b)

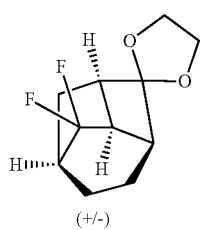 [SMILES: FC1(F)[C@H]2CC[C@H]3[C@@H]1[C@@H](C2)C31OCCO1]

(+/−)

Compound 1F (10 g, 0.051 mol) was dissolved in dichloromethane (120 mL), and cooled to 0° C. in an ice bath, and a solution of diethylaminosulphur trifluoride (41.495 g, 0.257 mol) diluted in dichloromethane (15 mL) was added thereto. The ice bath was removed, and the temperature was gradually raised until reflux, the temperature was maintained at which a reaction was allowed to proceed for 5 h. After cooling to room temperature, the reaction solution was poured into a saturated solution of sodium hydrogen carbonate at 0° C., and extracted with dichloromethane (80 mL×3). The organic layer was dried over anhydrous sodium sulfate, filtered, and concentrated under reduced pressure. The residue was purified by column chromatography (petroleum ether/ethyl acetate (v/v)=50:1), to give 4b (7.795 g, yield 70%) as brown oil.

$^1$H NMR (400 MHz, CDCl$_3$) δ 3.99-3.81 (m, 4H), 2.87-2.78 (m, 1H), 2.78-2.67 (m, 1H), 2.64-2.52 (m, 1H), 2.33-2.23 (m, 1H), 2.21-2.09 (m, 1H), 2.07-1.96 (m, 1H), 1.86-1.73 (m, 1H), 1.69 (dd, 1H), 1.67-1.55 (m, 1H), 1.55-1.43 (m, 1H).

$^{19}$F NMR (400 MHz, CDCl$_3$): δ−97.64 (d, J=226.1 Hz), −118.44 (d, J=226.1 Hz). LC-MS m/z (ESI): 217.1 [M+1]$^+$.

Step 2: (1R,3S,6S,8R)-7,7-difluorotricyclo[4.2.1.0$^{3,8}$]nonan-2-one(+/−) (4c)

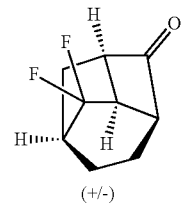

(+/−)

Compound 4b (7.79 g, 0.036 mol) was dissolved in a mixed solution of tetrahydrofuran (32 mL) and water (11 mL), trifluoroacetic acid (32 mL) was added dropwise and the temperature was raised to 70° C. to carry out a reaction for 6 hours. The mixture was cooled to room temperature and then to 0° C., adjusted to a neutral pH by addition of a sodium hydroxide solution (2 mol/L), and extracted with ethyl acetate (50 mL×3). The organic layer was dried over anhydrous sodium sulfate and concentrated under reduced pressure to obtain 4c as a light yellow solid (4.82 g, yield 70%).

$^1$H NMR (400 MHz, CDCl$_3$): δ 3.58-3.39 (m, 2H), 2.92 (dddd, 1H), 2.47 (ddd, 1H), 2.42-2.29 (m, 1H), 2.28-2.15 (m, 1H), 1.85-1.66 (m, 1H), 1.66-1.47 (m, 3H).

$^{19}$F NMR (400 MHz, CDCl$_3$): (5-96.49 (d, J=228.2 Hz), −116.83 (d, J=228.7 Hz).

Step 3: Ethyl 2-41R,3S,6S,8R)-7,7-difluorotricyclo[4.2.1.0$^{3,8}$]nonan-2-ylidene)acetate(+/−) (4d)

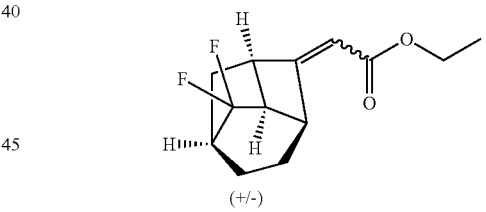

(+/−)

Sodium hydride (1.34 g, 0.034 mol) was added to dry tetrahydrofuran (50 mL), stirred and cooled to −5° C. in an ice bath. Triethyl phosphonoacetate (7.53 g, 0.034 mol) was added dropwise, and the temperature was maintained at which a reaction was allowed to proceed for 15 minutes. Then 4c (4.82 g, 0.028 mol) was slowly added dropwise, and the ice bath was removed, followed by a reaction at room temperature for 2 h. The reaction solution was cooled to 0° C., and a saturated ammonium chloride solution was slowly added dropwise to adjust the pH to about 7. 20 mL water was added, and the mixture was extracted with ethyl acetate (50 mL×3). The organic layer was dried over anhydrous sodium sulfate, and concentrated under reduced pressure. The concentrate was purified by column chromatography (petroleum ether/ethyl acetate (v/v)=20:1), to give 4d (4.75 g, yield 70%) as a light yellow oil.

LC-MS m/z (ESI): 243.1 [M+1]+.

Step 4: Ethyl 2-((1R,2R,3 S,6S,8R)-7,7-difluoro-2-(nitromethyl)tricyclo[4.2.1.0³,⁸]nonan-2-yl)acetate (+/−) (Intermediate 4)

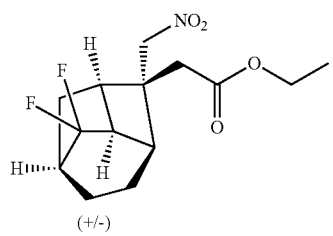 [SMILES: CCOC(=O)C[C@]1(C[N+](=O)[O-])[C@@H]2C[C@@H]3CC[C@H]1[C@H]2C3(F)F]

(+/−)

At room temperature, 4d (4.75 g, 0.02 mol) was added to a three-necked flask and nitromethane (7 mL) and 1,8-diazabicycloundec-7-ene (DBU) (5.97 g, 0.039 mol) were added. Then the temperature was raised to 85° C. to carry out a reaction for 4 hours, and then lowered to room temperature. The reaction system was poured into ice water and extracted with dichloromethane (20 mL×3). The organic layer was dried over anhydrous sodium sulfate, and concentrated under reduced pressure to obtain a crude product, which was purified by column chromatography (petroleum ether/ethyl acetate (v/v)=200:1 to 30:1), to give Intermediate 4 (4.04 g, yield 68%) as a yellow oil.

¹H NMR (400 MHz, CDCl₃) δ 4.82 (q, 2H), 4.20-4.11 (m, 2H), 2.96-2.82 (m, 1H), 2.72 (dd, 1H), 2.64 (dt, 3H), 2.42-2.15 (m, 3H), 1.92-1.79 (m, 1H), 1.78-1.65 (m, 1H), 1.56 (dd, 1H), 1.51-1.38 (m, 1H), 1.31-1.20 (m, 3H).

¹⁹F NMR (400 MHz, CDCl₃) δ 170.77, 134.05, 131.53, 129.01, 81.42, 60.77, 42.00, 40.22, 38.97, 32.54, 30.09, 27.81, 16.63, 14.08.

¹⁹F NMR (400 MHz, CDCl₃) δ−100.34 (d, J=229.9 Hz), −121.37 (d, J=229.9 Hz). LC-MS m/z (ESI): 326.0 [M+Na]+.

Intermediate 4 (4.04 g) was used for chiral resolution, and two optical isomers were obtained after the separation: Intermediate 4-1 (retention time: 17.2 min, 2.0 g, colorless transparent liquid, ee %=99%), and Intermediate 4-2 (retention time: 23.5 min, 2.0 g, colorless transparent liquid, ee %=99%).

Preparation conditions: Instrument: Gilson GX-281; Column: CHIRALPAK AD-H, 20×250 mm ID, 5 μm; Mobile phase: A for n-hexane and B for ethanol; Isocratic: A 50%; Flow rate: 12 mL/min; Back pressure: 1000 PSI; Column temperature: 30° C.; Wavelength: 210 nm; Cycle: 35 min; Sample preparation: the compound was dissolved in ethanol; Injection: 850 mg/syringe.

Intermediate 5

Ethyl 2-((1R,3S,6S,8R)-7-methylene-2-(nitromethyl)tricyclo[4.2.1.0]nonan-2-yl)acetate

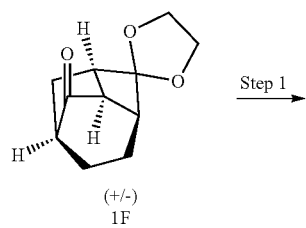

(+/−)
1F

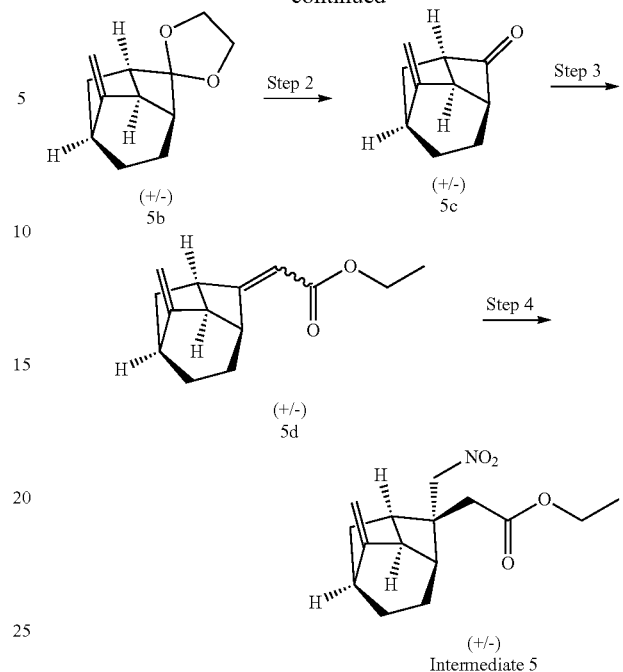

Step 1: (+/−) (1R,3S,6S,8R)-7-methylenespiro[tricyclo[4.2.1.0³,⁸]nonane-2,2'-[1,3]dioxolane] (Compound 5b)

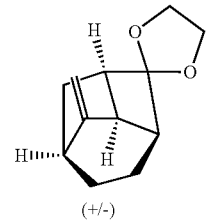

(+/−)

Methyl(triphenyl)phosphonium bromide (55.2 g, 154 mmoL) and 300 ml dry tetrahydrofuran were added to a reaction flask, and cooled to 0° C. under N₂ protection. Potassium t-butoxide (17.3 g, 154 mmol) was added in batches. After the addition, the temperature was held for 5 minutes, then raised to room temperature to carry out a reaction for 30 minutes, and then lowered to 0° C. A solution of Compound 1F in 100 ml tetrahydrofuran was added dropwise, and the temperature was raised to room temperature to carry out a reaction for 1 h, and then lowered to 0° C. A saturated aqueous ammonium chloride solution was added dropwise to adjust the pH to neutral. A 100 ml saturated aqueous solution of sodium chloride was added, and the mixture was extracted with ethyl acetate (200 ml*3). The organic layers were combined, dried, filtered, and concentrated to give 5b (9.6 g, yield 97%) as a light yellow liquid.

¹H NMR (400 MHz, CDCl₃) δ 4.80-4.73 (d, 2H), 3.93-3.85 (m, 4H), 2.82-2.76 (m, 3H), 2.58-2.54 (m, 1H), 2.03-1.96 (m, 1H), 1.76-1.66 (m, 3H), 1.43-1.32 (m, 2H).

Step 2: (+/−) (1R,3S,6S,8R)-7-methylenetricyclo[4.2.1.0³,⁸]nonan-2-one (Compound 5c)

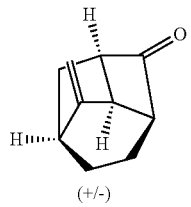

(+/−)

To a solution of Compound 5b (9.6 g, 0.050 mol, dissolved in 65 mL tetrahydrofuran and 22 mL purified water), trifluoroacetic acid (TFA) (13 mL) was added, and the mixture was stirred at 50° C. for 6 hours. The reaction mixture was cooled to 0° C., and the pH was adjusted to 7-8 by addition of sodium hydroxide (2 mol/1). The aqueous layer was extracted with ethyl acetate (2×150 mL). The organic phases were combined, dried over anhydrous sodium sulfate, and concentrated to give yellow oily 5c (8.0 g, 100%).

$^1$H NMR (400 MHz, CDCl$_3$) δ 4.97-4.92 (d, 2H), 3.52-3.40 (m, 2H), 3.06-3.09 (m, 1H), 2.72-2.68 (m, 1H), 2.18-2.11 (m, 1H), 1.91-1.85 (m, 1H), 1.59-1.56 (d, 1H), 1.55-1.50 (m, 1H), 1.44-1.32 (m, 2H). MS m/z (ESI): 149.1[M+1].

Step 3: (+/−) Ethyl (E)-2-((1R,3S,6S,8R)-7-methylenetricyclo[4.2.1.0³,⁸]nonan-2-ylidene)acetate (Compound 5d)

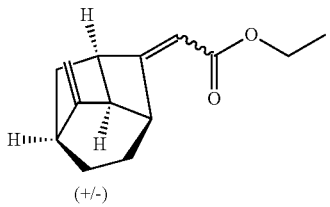 [SMILES: C=C1[C@H]2CC[C@@H]3C(=CC(=O)OCC)[C@H](C2)[C@H]13]

(+/−)

At 0° C., to a solution of sodium hydride (2.8 g, 0.070 mol) in tetrahydrofuran (100 mL), ethyl 2-(diethoxyphosphoryl)acetate (16.0 g, 0.070 mol) was added, and the mixture was stirred for 15 min. Then 5c (8.0 g, 0.054 mol) was added, and the reaction mixture was stirred at room temperature for 1 hour. The reaction mixture was cooled to 0° C., and a saturated ammonium chloride solution was added to adjust the pH to 7.0. Water (100 ml) was added, and the aqueous layer was extracted with ethyl acetate (3×100 ml). The organic phases were combined, dried over anhydrous sodium sulfate, and concentrated. The crude product was purified by column chromatography (petroleum ether/ethyl acetate (v/v)=20:1), to give 5d (8.9 g, 76%) as a yellow oil.

$^1$H NMR (400 MHz, CDCl$_3$) δ 5.67-5.56 (dt, 1H), 4.85-4.84 (d, 1H), 4.78-4.77 (dd, 1H), 4.20-4.10 (m, 2H), 3.83-3.68 (m, 1H), 3.34-3.24 (m, 1H), 3.09-3.02 (m, 1H), 2.66-2.62 (m, 1H), 2.10-1.92 (m, 2H), 1.81-1.69 (m, 1H), 1.54-1.43 (m, 3H), 1.30-1.25 (m, 3H).

Step 4: (+/−) ethyl 2-((1R,3 S,6S,8R)-7-methylene-2-(nitromethyl)tricyclo[4.2.1.0³,⁸]nonan-2-yl)acetate (Intermediate 5)

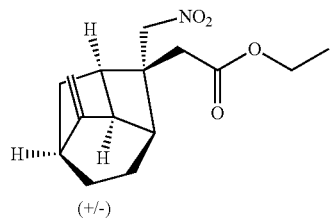 [SMILES: C=C1[C@H]2CC[C@H]3[C@@H]1[C@@H](C2)[C@]3(CC(=O)OCC)C[N+](=O)[O-]]

(+/−)

At 25° C., to a solution of 5d (8.6 g, 0.039 mol) in nitromethane (80 ml), 1,8-diazabicycloundec-7-ene (DBU) (12 g, 0.079 mol) was added. Then the reaction mixture was stirred at 85° C. for 4 hours, and then poured into ice water (200 ml), which was extracted with dichloromethane (3×200 ml). The organic phases were combined, dried over anhydrous sodium sulfate, and concentrated. The crude product was purified by column chromatography (petroleum ether/ethyl acetate (v/v)=200:1 to 30:1), to give Intermediate 5 (10.0 g, 90.9%) as a yellow oil.

$^1$H NMR (400 MHz, CDCl$_3$) δ 4.86 (q, 2H), 4.77 (dd, 2H), 4.15 (q, 2H), 3.17-3.05 (m, 1H), 2.75-2.59 (m, 5H), 2.15 (dt, 1H), 1.94 (dddd, 1H), 1.71 (ddd, 1H), 1.64-1.54 (m, 2H), 1.46-1.39 (m, 1H), 1.27 (t, 3H).

MS m/z (ESI): 280.1[M+1].

Intermediate 5 (10.0 g) was used for chiral resolution, and two optical isomers were obtained after the separation: Intermediate 5-1 (retention time: 10.4 min, 3.8 g, colorless transparent liquid, ee %=99%), and Intermediate 5-2 (retention time: 13.1 min, 3.8 g, colorless transparent liquid, ee %=99%).

Preparation conditions: Instrument: Gilson GX-281; Column: CHIRALPAK AD-H, 20×250 mm ID, 5 μm; Mobile phase: A for n-hexane and B for isopropyl alcohol; Isocratic: A 98%; Flow rate: 12 mL/min; Back pressure: 1000 PSI; Column temperature: 30° C.; Wavelength: 210 nm; Cycle: 17.3 min; Sample solution: Intermediate 5 was dissolved in isopropyl alcohol.

Intermediate 6

(+/−) t-butyl 2-((1R,2S,3S,6R,8R)-2-(nitromethyl)-tricyclo[4.2.1.0³,⁸]nonan-2-yl)acetate (Intermediate 6)

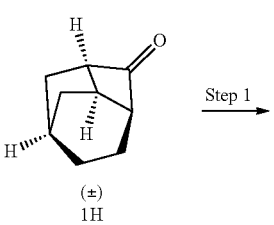

(±)
1H

Step 2: (+/−)-(1R,3S,6R,8R)-2-(nitromethyl)tricyclo[4.2.1.0³,⁸]nonane (6b)

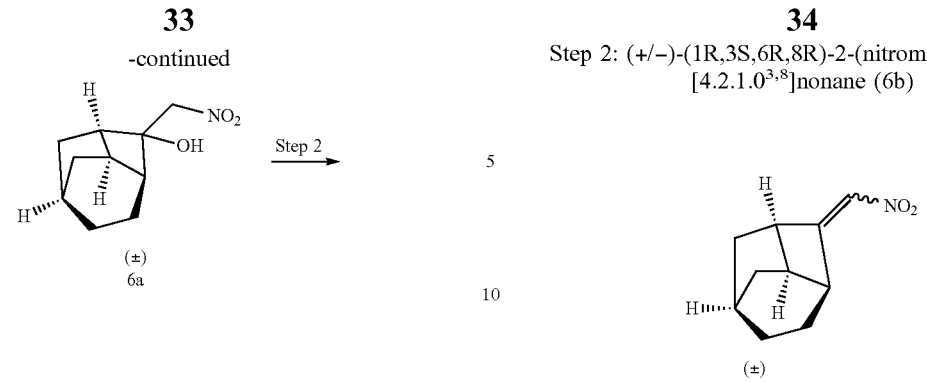

(±)

6a (0.50 g, 2.54 mmol), acetic anhydride (10 mL), and p-toluenesulfonic acid (0.44 g, 2.54 mmol) were added to a reaction flask, allowed to react at room temperature for 2 h, and then cooled to 0° C. A 50 ml saturated aqueous solution of sodium bicarbonate was added, followed by stirring for 1 hour. The mixture was extracted with dichloromethane (35 ml×3). The organic layers were combined, dried, filtered, and concentrated to obtain a colorless liquid (0.15 g) which was directly used in the next reaction, dissolved in methanol (8 ml) and cooled to 0° C. Sodium methoxide (0.03 g, 0.61 mmol) was added, followed by a reaction at room temperature for 2 hours. A 20 ml saturated aqueous solution of ammonium chloride was added, and the mixture was extracted with dichloromethane (40 ml×3). The organic layers were combined, dried, filtered, and concentrated. The concentrate was purified by silica gel column chromatography (petroleum ether/ethyl acetate (v/v)=100:1), to give 6b (0.08 g, yield 74.1%) as a yellow oil.

¹H NMR (400 MHz, CDCl₃) δ 6.87 (dd, 1H), 3.94-3.61 (m, 1H), 3.25 (ddd, 1H), 3.01-2.80 (m, 1H), 2.39 (td, 1H), 2.12-1.76 (m, 4H), 1.73-1.51 (m, 2H), 1.48-1.23 (m, 4H).

Step 3: (+/−) t-butyl 2-41R,2S,3S,6R,8R)-2-(nitromethyl)-tricyclo[4.2.1.0³,⁸]nonan-2-yl)acetate (Intermediate 6)

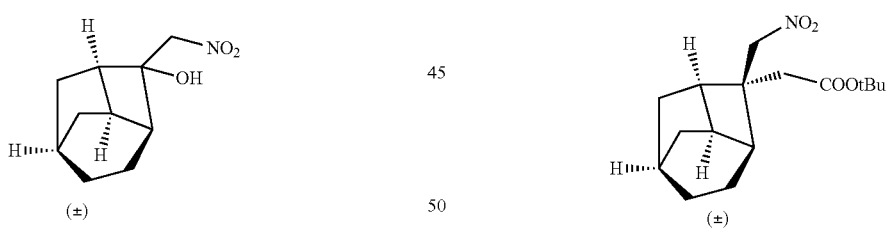

(±)

1 M lithium bis(trimethylsilyl)amide (290 mL, 0.29 mol) was added to a reaction flask, and cooled to −60° C. under N₂ protection. A solution of t-butyl acetate (33.62 g, 0.29 mmol) in tetrahydrofuran (150 mL) was added dropwise, followed by stirring for 20 min. A solution of 6b (28.82 g, 0.16 mol) in tetrahydrofuran (250 mL) was added dropwise, followed by a reaction at −60° C. for 2 hours. A saturated aqueous solution of ammonium chloride (400 ml) was added, and the mixture was extracted with ethyl acetate (200 ml×3). The organic layers were combined, dried, filtered, and concentrated. The concentrate was purified by silica gel column chromatography (petroleum ether/ethyl acetate (v/v) =100:1), to give Intermediate 6 (39.4 g, yield 84.8%) as a colorless liquid, which was used for chiral resolution. Two optical isomers were obtained after the separation: Intermediate 6-1 (retention time: 2.5 min, 9.33 g), and Intermediate 6-2 (retention time: 3.2 min, 8.68 g).

Preparation conditions for chiral resolution: instrument: Waters UPC2 analytical SFC (SFC-H); column: ChiralPak AD, 150×4.6 mm ID, 3 μm; mobile phase: A for CO2 and B for EtOH (0.05% DEA); Gradient: B 5-40%; flow rate: 2.5 mL/min; column temperature: 35° C.

Intermediate 6-1: $^1$H NMR (400 MHz, CDCl$_3$) δ 4.74 (q, 2H), 2.86 (dt, 1H), 2.75-2.63 (m, 2H), 2.53 (ddd, 1H), 2.31 (tt, 2H), 2.05 (dt, 1H), 1.84-1.73 (m, 1H), 1.68-1.55 (m, 4H), 1.52 (dd, 1H), 1.48-1.40 (m, 9H), 1.31-1.23 (m, 1H).

Intermediate 6-2: $^1$H NMR (400 MHz, CDCl$_3$) δ 4.74 (q, 1H), 2.89-2.81 (m, 1H), 2.75-2.63 (m, 2H), 2.53 (ddd, 1H), 2.32 (tt, 1H), 2.04 (dd, 1H), 1.82-1.75 (m, 1H), 1.70-1.56 (m, 4H), 1.52 (dd, 1H), 1.49-1.43 (m, 9H), 1.31-1.21 (m, 1H).

Example 1 (±)-2-41R,2R,3 S,6R,8R)-2-(aminomethyl)tricyclo[4.2.1.0$^{3,8}$]nonan-2-yl)acetic acid (Compound 1)

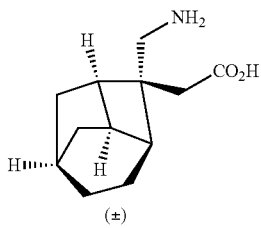

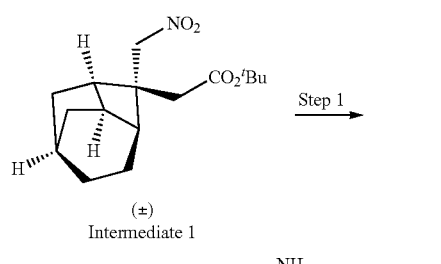

Intermediate 1

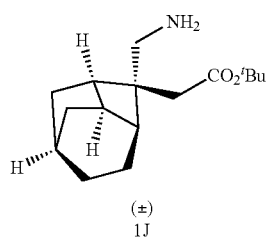

1J

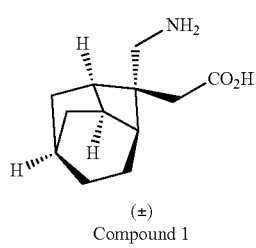

Compound 1

Step 1: (±)-tert-butyl 2-((1R,2R,3S,6R,8R)-2-(aminomethyl)tricyclo[4.2.1.0$^{3,8}$]nonan-2-yl)acetate (1J)

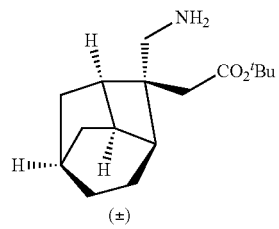 [SMILES: CC(C)(C)OC(=O)C[C@]1(CN)[C@@H]2C[C@@H]3CC[C@H]1[C@H]2C3]

(±)-tert-butyl 2-((1R,2R,3S,6R,8R)-2-(nitromethyl)tricyclo[4.2.1.0$^{3,8}$]nonan-2-yl)acetate (Intermediate 1) (5 g, 18.7 mmol), ethanol (40 mL), water (20 mL), reduced iron powder (6.05 g, 108 mmol) and ammonium chloride (5.62 g, 108 mmol) were sequentially added to a reaction flask, followed by a reaction under reflux for 6 hours. The reaction solution was cooled, filtered by suction, and washed with ethyl acetate (50 L×3). The filtrate was collected and concentrated under reduced pressure, and the aqueous phase was extracted with ethyl acetate (10 L×3). The organic phase was dried over anhydrous sodium sulfate and filtered. The filtrate was concentrated under reduced pressure. The residue was purified by silica gel column chromatography (dichloromethane/methanol (v/v)=40:1-10:1), to give (±)-tert-butyl 2-41R,2R,3S,6R,8R)-2-(aminomethyl)tricyclo[4.2.1.0$^{3,8}$]nonan-2-yl)acetate (1J) (4.1 g, yield 93%) as a white solid.

$^1$H NMR (400 MHz, CDCl$_3$) δ 3.42-3.26 (m, 2H), 2.88 (dd, J=12.9, 5.3 Hz, 1H), 2.61-2.46 (m, 3H), 2.35-2.23 (m, 2H), 2.06-1.91 (m, 1H), 1.81-1.66 (m, 1H), 1.65-1.35 (m, 14H), 1.27-1.17 (m, 1H).

Step 2: (±)-2-41R,2R,3S,6R,8R)-2-(aminomethyl)tricyclo[4.2.1.0$^{3,8}$]nonan-2-yl)acetic Acid (Compound 1)

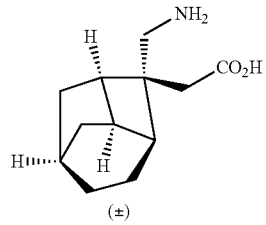 [SMILES: NC[C@@]1(CC(=O)O)[C@@H]2C[C@@H]3CC[C@H]1[C@H]2C3]

(±)-tert-butyl 2-((1R,2R,3S,6R,8R)-2-(aminomethyl)tricyclo[4.2.1.0$^{3,8}$]nonan-2-yl)acetate (1J) (4 g, 15 mmol) and dichloromethane (30 mL) were added to a reaction flask, and trifluoroacetic acid (20 mL) was added dropwise thereto in an ice bath, followed by a reaction at room temperature for 4 hours and by concentration under reduced pressure until dryness. The resultant crude product was dissolved in water (100 ml), to which aqueous ammonia was added to adjust the pH to 7-8, followed by suction filtration under reduced pressure. The resultant was washed with water (50 mL×3) and dichloromethane (50 mL×3), and oven-dried to give (±)-2-((1R,2R,3S,6R,8R)-2-(aminomethyl)tricyclo[4.2.1.0$^{3,8}$]nonan-2-yl)acetic acid (Compound 1) (2.7 g, yield 87%) as a white solid.

MS m/z (ESI): 210.3[M+1].

$^1$H NMR (400 MHz, D$_2$O) δ 3.31-3.15 (m, 2H), 2.81 (s, 1H), 2.56-2.33 (m, 3H), 2.26 (d, 1H), 2.09-1.86 (m, 2H), 1.77-1.41 (m, 5H), 1.41-1.28 (m, 1H), 1.25-1.11 (m, 1H).

Example 2 (±)-2-41R,2R,3S,6R,8R)-2-(aminomethyl)tricyclo[4.2.1.0$^{3,8}$]nonan-2-yl)acetic acid benzenesulfonic acid (1:1) (Compound 2)

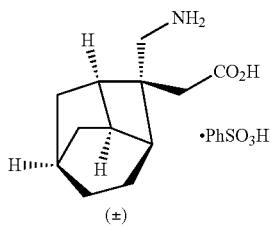 [SMILES: "·PhSO3H" ; NC[C@@]1(CC(=O)O)[C@@H]2C[C@@H]3CC[C@H]1[C@H]2C3]

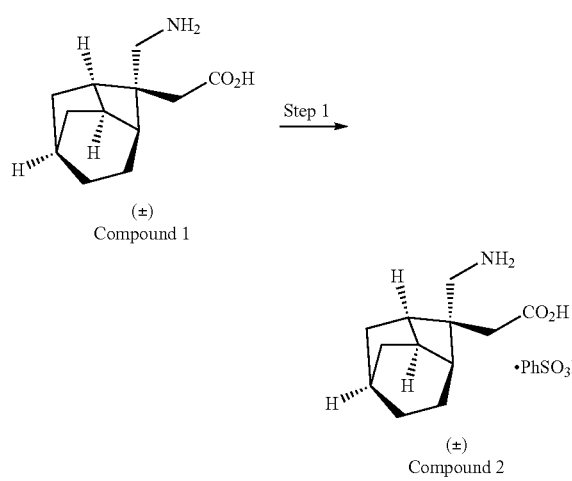

Step 1: (±)-2-((1R,2R,3S,6R,8R)-2-(aminomethyl)tricyclo[4.2.1.0$^{3,8}$]nonan-2-yl)acetic acid benzenesulfonic acid (1:1) (Compound 2)

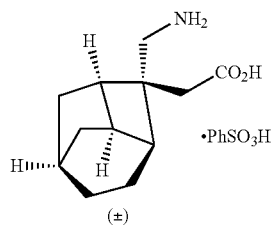

(±)-2-41R,2R,3 S,6R,8R)-2-(aminomethyl)tricyclo [4.2.1.0$^{3,8}$]nonan-2-yl)acetic acid (Compound 1) (1 g, 4.7 mmol) and methanol (50 mL) were added to a reaction flask, a solution of benzenesulfonic acid in methanol (1.13 g, 7.2 mmol) was added dropwise, followed by stirring at room temperature for 1 hour. The reaction solution was concentrated and made into a slurry with ethyl acetate (50 mL), followed by suction filtration under reduced pressure. The resultant was washed with ethyl acetate (30 mL×3) and oven-dried to give (±)-2-((1R, 2R,3 S,6R,8R)-2-(aminomethyl)tricyclo[4.2.1.0$^{3,8}$]nonan-2-yl)acetic acid benzenesulfonic acid (1:1) (Compound 2) (1.4 g, yield 80%) as a white solid.

$^1$H NMR (400 MHz, D$_2$O) δ 7.86-7.68 (m, 2H), 7.64-7.43 (m, 3H), 3.34 (s, 2H), 2.81 (dd, 1H), 2.57 (q, 2H), 2.46-2.36 (m, 1H), 2.26 (dd, 1H), 2.17-2.05 (m, 1H), 1.96 (dt, 1H), 1.79-1.65 (m, 1H), 1.65-1.39 (m, 4H), 1.33 (dd, J=13.5, 8.7 Hz, 1H), 1.25-1.14 (m, 1H).

Example 3. Preparation of Compound 3 2-41R,2R,3S,6R,8R)-2-(aminomethyl)tricyclo[4.2.1.0$^{3,8}$]nonan-2-yl)acetic Acid (Compound 3)

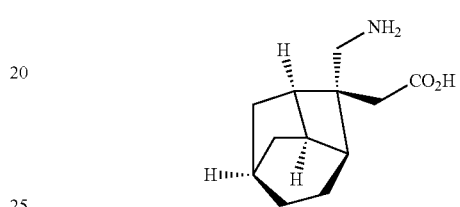

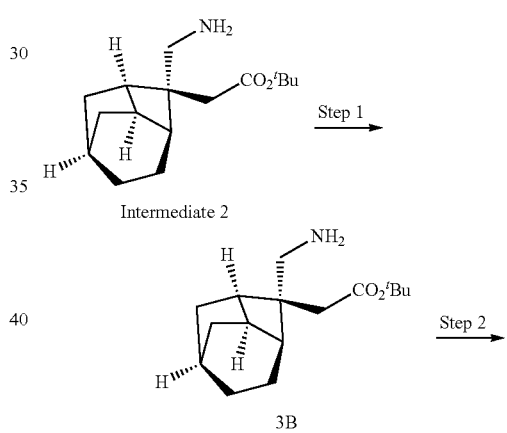

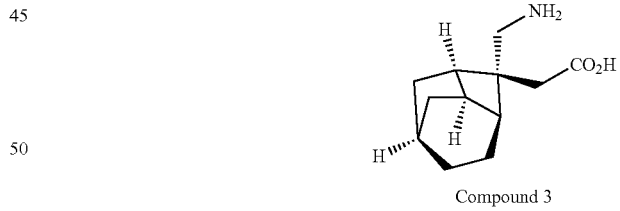

Step 1: Intermediate 2 (0.62 g, 2.1 mmol), ethanol (6 mL), water (3 mL), reduced iron powder (0.7 g, 13 mmol) and ammonium chloride (0.67 g, 13 mmol) were sequentially added to a reaction flask, followed by a reaction under reflux for 6 hours. The reaction solution was cooled, filtered by suction, washed with ethyl acetate (20 mL×3), and concentrated under reduced pressure, and the aqueous phase was extracted with ethyl acetate (20 ml×3). The organic phases were combined, dried over anhydrous sodium sulfate and filtered. The filtrate was concentrated under reduced pressure. The residue was purified by silica gel column chromatography (dichloromethane/methanol (v/v)=40:1-10:1), to give 3B (0.45 g, yield 85%) as a white solid.

Step 2: 3B (0.45 g, 1.7 mmol) and dichloromethane (5 mL) were added to a reaction flask, and trifluoroacetic acid (5 mL) was added dropwise thereto in an ice bath, followed by a reaction at room temperature for 4 hours and by concentration under reduced pressure. The resultant crude product was dissolved in water (10 ml), to which aqueous ammonia was added to adjust the pH to 7-8, followed by suction filtration under reduced pressure. The resultant was washed with water (10 mL×3) and dichloromethane (20 mL×3), and oven-dried to give Compound 3 (0.27 g, yield 80%) as a white solid.

$^1$H NMR (400 MHz, D$_2$O): δ 3.31-3.15 (m, 2H), 2.81 (s, 1H), 2.56-2.33 (m, 3H), 2.26 (d, J=6.0 Hz, 1H), 2.09-1.86 (m, 2H), 1.77-1.41 (m, 5H), 1.41-1.28 (m, 1H), 1.25-1.11 (m, 1H).

LC-MS m/z (ESI): 210.3 [M+1]$^+$.

Example 4. Preparation of Compound 4

Step 1: Compound 3 (0.27 g, 1.29 mmol) and methanol (10 mL) were added to a reaction flask, a solution of benzenesulfonic acid in methanol (0.3 g, 1.94 mmol) was added dropwise, followed by stirring at room temperature for 1 hour. The reaction mixture was concentrated and made into a slurry with ethyl acetate (30 mL), followed by suction filtration under reduced pressure. The resultant was washed with ethyl acetate (10 mL×3) and oven-dried to give Compound 4 (the 1:1 benzenesulfonate of Compound 3) (0.43 g, yield 90%) as a white solid.

$^1$H NMR (400 MHz, D$_2$O) δ 7.85-7.70 (m, 2H), 7.54 (tt, 3H), 3.33 (d, 2H), 2.81 (dd, 1H), 2.57 (q, 2H), 2.47-2.37 (m, 1H), 2.27 (dd, 1H), 2.17-2.06 (m, 1H), 1.96 (dd, 1H), 1.79-1.66 (m, 1H), 1.66-1.40 (m, 4H), 1.33 (dd, 1H), 1.26-1.15 (m, 1H).

Example 5. Preparation of Compound 5 2-((1S,2S, 3R,6S,8S)-2-(aminomethyl)tricyclo[4.2.1.0$^{3,8}$] nonan-2-yl)acetic Acid (Compound 5)

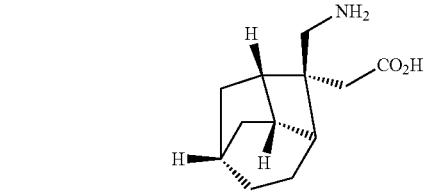

Intermediate 3

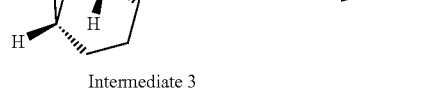

Step 1

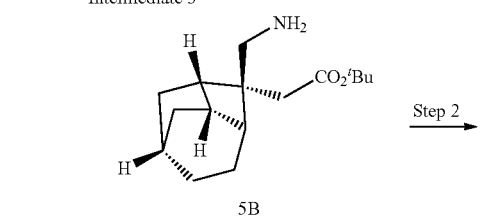

5B

Step 2

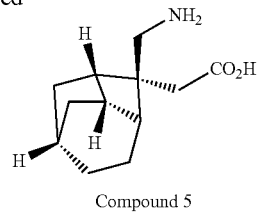

Compound 5

Step 1: Intermediate 3 (0.61 g, 2.1 mmol), ethanol (6 mL), and water (3 mL) were sequentially added to a reaction flask, and then reduced iron powder (0.69 g, 12 mmol) and ammonium chloride (0.66 g, 12 mmol) were sequentially added thereto, followed by a reaction under reflux for 6 hours. The reaction solution was cooled, filtered by suction, washed with ethyl acetate (20 mL×3), and concentrated under reduced pressure, and the aqueous phase was extracted with ethyl acetate (20 ml×3). The organic phase was dried over anhydrous sodium sulfate and filtered. The filtrate was concentrated under reduced pressure. The residue was purified by silica gel column chromatography (dichloromethane/methanol (v/v)=40:1-10:1), to give 5B (0.4 g, yield 73%) as a white solid.

Step 2: 5B (0.4 g, 1.5 mmol) and dichloromethane (5 mL) were added to a reaction flask, and trifluoroacetic acid (5 mL) was added dropwise thereto in an ice bath, followed by a reaction at room temperature for 4 hours and by concentration under reduced pressure. The resultant crude product was dissolved in water (10 ml), to which aqueous ammonia was added to adjust the pH to 7-8, followed by suction filtration under reduced pressure. The resultant was washed sequentially with water (10 mL×3) and dichloromethane (20 mL×3), and oven-dried to give Compound 5 (0.2 g, yield 64%) as a white solid.

$^1$H NMR (400 MHz, D$_2$O): δ 3.31-3.15 (m, 2H), 2.81 (s, 1H), 2.56-2.33 (m, 3H), 2.26 (d, J=6.0 Hz, 1H), 2.09-1.86 (m, 2H), 1.77-1.41 (m, 5H), 1.41-1.28 (m, 1H), 1.25-1.11 (m, 1H).

LC-MS m/z (ESI): 210.3[M+1]+.

Example 6. Preparation of Compound 6

Step 1: Compound 5 (0.2 g, 0.96 mmol) and methanol (10 mL) were added to a reaction flask, a solution of benzenesulfonic acid in methanol (0.23 g, 1.4 mmol) was added dropwise, followed by stirring at room temperature for 1 hour. The resultant was concentrated and made into a slurry with ethyl acetate (30 mL), followed by suction filtration under reduced pressure. The resultant was washed with ethyl acetate (10 mL×3) and oven-dried to give Compound 6 (the 1:1 benzenesulfonate of Compound 5) (0.33 g, yield 90%) as a white solid.

$^1$H NMR (400 MHz, D$_2$O) δ 7.85-7.70 (m, 2H), 7.54 (tt, 3H), 3.33 (d, 2H), 2.81 (dd, 1H), 2.57 (q, 2H), 2.47-2.37 (m, 1H), 2.27 (dd, 1H), 2.17-2.06 (m, 1H), 1.96 (dd, 1H), 1.79-1.66 (m, 1H), 1.66-1.40 (m, 4H), 1.33 (dd, 1H), 1.26-1.15 (m, 1H).

Example 7. Preparation of Compound 7 2-(4-(aminomethyl)tricyclo[3.2.1.0³,⁶]octan-4-yl)acetic Acid (Compound 7)

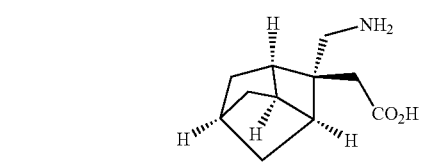 [SMILES: NC[C@@]1(CC(=O)O)[C@@H]2C[C@H]3C[C@@H]2[C@@H]1C3]

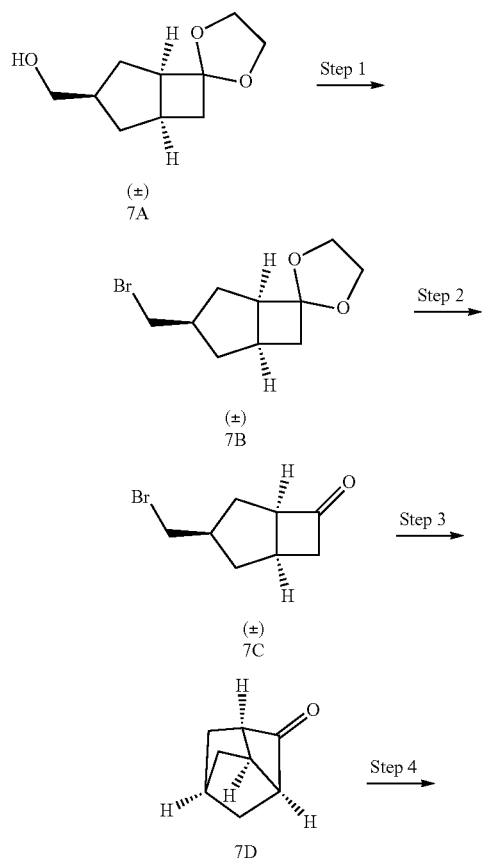

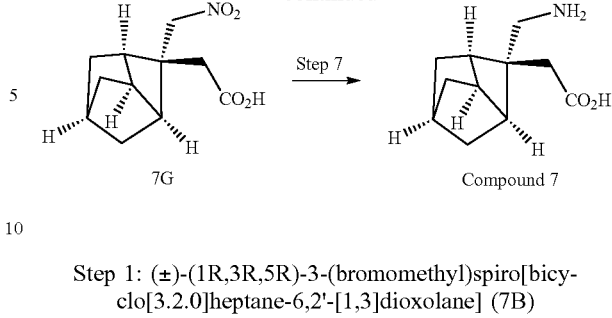

Step 1: (±)-(1R,3R,5R)-3-(bromomethyl)spiro[bicyclo[3.2.0]heptane-6,2'-[1,3]dioxolane] (7B)

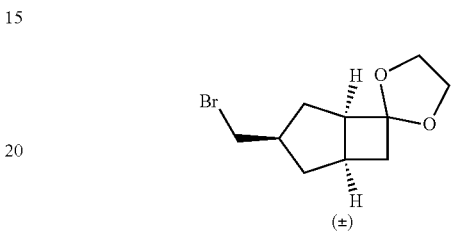

(±)-(1R,3R,5R)-spiro[bicyclo[3.2.0]heptane-6,2'-[1,3]dioxolan]-3-ylmethanol (7A) (which can be prepared with reference to WO2017107907) (6.0 g, 32.6 mmol), carbon tetrabromide (32.4 g, 97.7 mmol) and tetrahydrofuran (163 mL) were added to a reaction flask, and cooled to 0° C. Triphenylphosphine (25.6 g, 97.7 mmol) was added thereto. The mixture was stirred at 0° C. for 30 min, and then warmed to room temperature to carry out a reaction for 4 hours. A saturated sodium chloride solution (50 mL) was added and the mixture was extracted with ethyl acetate (50 mL×3). The organic layers were combined, dried over anhydrous sodium sulfate and filtered. The filtrate was concentrated under reduced pressure. The residue was purified by silica gel column chromatography (petroleum ether/ethyl acetate (v/v)=100:1), to give (±)-(1R,3R,5R)-3-(bromomethyl)spiro[bicyclo[3.2.0]heptane-6,2'-[1,3]dioxolane] (7B) (6.80 g, yield 84.5%) as a colorless liquid.

$^1$H NMR (400 MHz, CDCl$_3$) δ3.97-3.68 (m, 4H), 3.56-3.39 (m, 2H), 2.94-2.84 (m, 1H), 2.61-2.33 (m, 3H), 2.23-1.81 (m, 3H), 1.82-1.61 (m, 1H), 1.47-1.23 (m, 1H).

MS m/z (ESI): 269.0 (M+23).

Step 2: (±)-(1R,3R,5R)-3-(bromomethyl)bicyclo[3.2.0]heptan-6-one (7C)

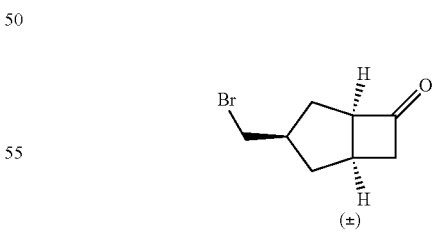

(±)-(1R,3R,5R)-3-(bromomethyl)spiro[bicyclo[3.2.0]heptane-6,2'-[1,3]dioxolane] (7B) (11.3 g, 45.7 mmol), tetrahydrofuran (90 mL) and water (30 mL) were sequentially added to a reaction flask and cooled to 0° C. Trifluoroacetic acid (30 mL) was added dropwise and the temperature was raised to 35° C. to carry out a reaction for 1.5 hours. The mixture was cooled in an ice-water bath, adjusted to a neutral pH by addition of a saturated sodium bicarbonate solution, and extracted with ethyl acetate (25 mL×3). The organic phase was dried over anhydrous sodium sulfate and filtered. The filtrate was concentrated under reduced pressure. The residue was purified by silica gel column chromatography (petroleum ether/ethyl acetate (v/v)=100:1-50:1-10:1), to give (±)-(1R,3R,5R)-3-(bromomethyl)bicyclo[3.2.0]heptan-6-one (7C) (8.10 g, yield 87.2%) as a colorless oily liquid.

$^1$H NMR (400 MHz, CDCl$_3$) δ 3.78-3.60 (m, 1H), 3.48-3.18 (m, 3H), 2.95-2.83 (m, 1H), 2.78-2.31 (m, 3H), 2.13-1.97 (m, 1H), 1.83-1.69 (m, 1H), 1.50-1.29 (m, 1H).

MS m/z (ESI): 225.0 (M+23).

Step 3: tricyclo[3.2.1.0$^{3,6}$]octan-4-one (7D)

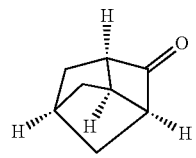

Potassium t-butoxide (6.71 g, 59.8 mmol) and toluene (400 mL) were added to a reaction flask, and the system was cooled to −15° C., to which a solution of (±)-(1R,3R,5R)-3-(bromomethyl)bicyclo[3.2.0]heptan-6-one (7C) (8.10 g, 39.9 mmol) in toluene (20 mL) was added dropwise, followed by a reaction at 0° C. for 2 hours. A saturated ammonium chloride solution (250 mL) was added and the mixture was allowed to partition. The organic phase was dried over anhydrous sodium sulfate and filtered. The filtrate was concentrated under reduced pressure. The residue was purified by silica gel column chromatography (petroleum ether/ethyl acetate (v/v)=100:1, 50:1), to give tricyclo[3.2.1.0$^{3,6}$]octan-4-one (7D) (1.40 g, yield 28.7%) as a colorless liquid.

$^1$H NMR (400 MHz, CDCl$_3$) δ 2.96 (dd, 2H), 2.71-2.63 (m, 1H), 2.53 (d, 1H), 1.99-1.87 (m, 4H), 1.68 (d, 2H).

MS m/z (ESI): 123.1 (M+1).

Step 4: ethyl 2-(tricyclo[3.2.1.0$^{3,6}$]octan-4-ylidene)acetate (7E)

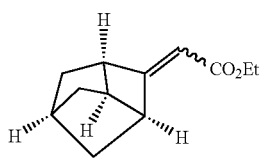 [SMILES: CCOC(=O)C=C1[C@H]2C[C@@H]3C[C@H]2[C@H]1C3]

Sodium hydride (0.27 g, 9.82 mmol) and tetrahydrofuran (50 mL) were added to a reaction flask and cooled to 0° C. A solution of Triethylphosphonoacetate (2.02 g, 9.00 mmol) in tetrahydrofuran (1 mL) was added dropwise, followed by stirring at 0° C. for 30 min. A solution of tricyclo[3.2.1.0$^{3,6}$]octan-4-one (7D) (1.00 g, 8.19 mmol) in tetrahydrofuran (5 mL) was added dropwise, and the temperature was raised to room temperature, followed by stirring for 1.5 hours. A saturated ammonium chloride solution (10 mL) was added and the mixture was extracted with ethyl acetate (50 mL×3). The organic phase was dried over anhydrous sodium sulfate and filtered. The filtrate was concentrated under reduced pressure. The residue was purified by silica gel column chromatography (petroleum ether/ethyl acetate (v/v)=100:1), to give ethyl 2-(tricyclo[3.2.1.0$^{3,6}$]octan-4-ylidene)acetate (7E) (1.40 g, yield 89.0%) as a colorless oily liquid.

$^1$H NMR (400 MHz, CDCl$_3$) δ 5.32 (s, 1H), 4.14 (q, 2H), 3.46 (td, 1H), 2.89-2.72 (m, 2H), 2.52 (dd, 1H), 1.88-1.75 (m, 3H), 1.71 (d, 1H), 1.50 (s, 2H), 1.26 (t, 3H). MS m/z (ESI): 215.1 (M+23).

Step 5: ethyl 2-(4-(nitromethyl)tricyclo[3.2.1.0$^{3,6}$]octan-4-yl)acetate (7F)

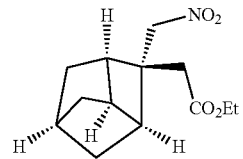 [SMILES: CCOC(=O)C[C@]1(C[N+](=O)[O-])[C@@H]2C[C@H]3C[C@@H]2[C@@H]1C3]

Ethyl 2-(tricyclo[3.2.1.0$^{3,6}$]octan-4-ylidene)acetate (7E) (1.40 g, 7.28 mmol), nitromethane (50 mL) and 1,5-diazabicyclo[5.4.0]undec-5-ene (5.54 g, 36.4 mmol) were added to a reaction flask, followed by a reaction at 80° C. for 7 hours. After cooling to room temperature, water (30 ml) was added, and the mixture was extracted with ethyl acetate (30 mL×3). The organic phase was dried over anhydrous sodium sulfate and filtered. The filtrate was concentrated under reduced pressure. The residue was purified by silica gel column chromatography (petroleum ether/ethyl acetate (v/v)= 400:1), to give ethyl 2-(4-(nitromethyl)tricyclo[3.2.1.0$^{3,6}$]octan-4-yl)acetate (7F) as (1.44 g, yield 78.1%) a colorless oily liquid.

$^1$H NMR (400 MHz, CDCl$_3$) δ 4.84 (s, 2H), 4.13 (q, 2H), 3.07 (td, 1H), 2.60 (s, 2H), 2.43 (s, 1H), 2.37-2.26 (m, 2H), 1.74 (d, 2H), 1.50-1.40 (m, 2H), 1.35 (s, 2H), 1.26 (t, 3H).

MS m/z (ESI): 276.1 (M+23).

Step 6: 2-(4-(nitromethyl)tricyclo[3.2.1.0$^{3,6}$]octan-4-yl)acetic acid (7G)

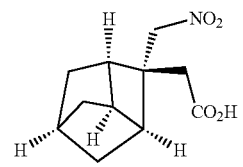

Ethyl 2-(4-(nitromethyl)tricyclo[3.2.1.0]octan-4-yl)acetate (7F) (1.44 g, 5.68 mmol), methanol (8 mL), an aqueous solution (3 ml) of sodium hydroxide (0.34 g, 8.53 mmol) were added to a reaction flask, and the mixture was heated to 60° C. to carry out a reaction for 5 hours. In an ice bath, 1 mol/L HCl was added dropwise thereto until pH=2, and the mixture was extracted with ethyl acetate (60 mL×3). The organic phases were combined, washed with water (60 mL×3), dried over anhydrous sodium sulfate and filtered. The filtrate was concentrated under reduced pressure. The residue was purified by silica gel column chromatography (dichloromethane/methanol (v/v)=100:1), to give 2-(4-(nitromethyl)tricyclo[3.2.1.0$^{3,6}$]octan-4-yl)acetic acid (7G) as (1.20 g, yield 93.7%) a white solid.

$^1$H NMR (400 MHz, MeOD) δ 3.15 (s, 2H), 3.03 (dd, J=5.6, 4.2 Hz, 1H), 2.49 (s, 2H), 2.40 (s, 1H), 2.19-2.09 (m, 2H), 1.89 (d, 2H), 1.44-1.32 (m, 4H).

MS m/z (ESI): 224.1 (M−1).

Step 7: 2-(4-(aminomethyl)tricyclo[3.2.1.0$^{3,6}$]octan-4-yl)acetic Acid (Compound 7)

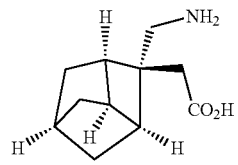

2-(4-(nitromethyl)tricyclo[3.2.1.0$^{3,6}$]octan-4-yl)acetic acid (7G) (1.20 g, 5.33 mmol), 25 mL methanol, platinum dioxide (0.20 g, 0.88 mmol) were added to a reaction flask, purged three times with hydrogen, and heated to 35° C. to carry out a reaction for 5 hours, followed by filtration. The filter cake was washed with 50° C. methanol (250 ml) and concentrated. Dichloromethane (60 ml) was added, and triethylamine was added to adjust pH=8. A slurry was made and filtered to obtain a solid filter cake, which was rinsed with dichloromethane (50 ml) to give 2-(4-(aminomethyl)tricyclo[3.2.1.0$^{3,6}$]octan-4-yl)acetic acid (Compound 7) (0.43 g, yield 41%) as a white solid.

$^1$H NMR (400 MHz, CD$_3$OD) δ 3.15 (s, 2H), 3.03 (dd, J=5.6, 4.2 Hz, 1H), 2.49 (s, 2H), 2.40 (s, 1H), 2.19-2.09 (m, 2H), 1.89 (d, 2H), 1.44-1.32 (m, 4H).

MS m/z (ESI): 196.1 (M+1).

Example 8

2-(4-(aminomethyl)tricyclo[3.2.1.0$^{3,6}$]octan-4-yl) acetic acid benzenesulfonic Acid (1:1) (Compound 8)

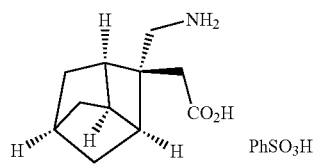 [SMILES: "PhSO3H" ; NC[C@@]1(CC(=O)O)[C@@H]2C[C@H]3C[C@@H]2[C@@H]1C3]

2-(4-(aminomethyl)tricyclo[3.2.1.0$^{3,6}$]octan-4-yl)acetic acid (Compound 7) (0.39 g, 2.0 mmol) and methanol (8 mL) were added to a reaction flask, a solution of benzenesulfonic acid (0.47 g, 3.0 mmol) in methanol (1 ml) was added dropwise, followed by a reaction at room temperature for 0.5 hours. The system was concentrated and made into a slurry with ethyl acetate (10 mL), followed by filtration to give 2-(4-(aminomethyl)tricyclo[3.2.1.0$^{3,6}$]octan-4-yl)acetic acid benzenesulfonic acid (1:1) (Compound 8) (0.61 g, yield 86%) as a white solid.

$^1$H NMR (400 MHz, MeOD) δ 7.92-7.69 (m, 2H), 7.42 (dd, 3H), 3.07 (s, 1H), 2.56 (s, 2H), 2.43 (s, 1H), 2.25-2.17 (m, 2H), 1.80 (d, 2H), 1.45 (d, 2H), 1.36 (s, 2H). MS m/z (ESI): 196.1 (M+1).

Example 9. Preparation of Compound 9

Step 1: At room temperature, Intermediate 4-2 (2 g, 6.6 mmol) was added to ethanol (15 mL), and ammonium chloride (1.76 g, 33 mmol), iron powder (1.84 g, 33 mmol), and water (7.5 mL) were sequentially added. After the addition, the temperature was raised to 90° C. to carry out a reaction for 6 hours. The mixture was cooled to room temperature, filtered, and rotary-dried under reduced pressure. 100 mL water was added and the mixture was extracted 3 times with 200 ml dichloromethane. The organic layer was dried over anhydrous sodium sulfate, and the organic solvent was rotary-evaporated under reduced pressure, to give 9B (1.45 g, yield 97%) as a white solid.

LC-MSm/z (ESI): 228.1[M+1]$^+$.

Step 2: Compound 9B (1.3 g, 5.7 mmol) was added to a 10 mL sodium hydroxide solution (6 mol/L) to carry out a reaction under reflux for 12 hours. The reaction solution was concentrated, 20 mL water was added, and the mixture was extracted twice with 20 mL dichloromethane. The aqueous phase was adjusted to a pH of about 7 with 6 mol/L HCl, and a large amount of white solid was formed, which was filtered to give Compound 9 (0.57 g, yield 40.7%) as a white solid.

$^1$H NMR (400 MHz, MeOD) δ 3.23-3.03 (m, 2H), 2.91-2.76 (m, 1H), 2.63-2.45 (m, 3H), 2.41 (dt, 1H), 2.37-2.28 (m, 1H), 2.18 (ddd, 2H), 1.97-1.82 (m, 1H), 1.83-1.67 (m, 2H), 1.65-1.49 (m, 1H).

$^{19}$F NMR (400 MHz, CDCl$_3$) (5-100.93 (d, J=230.0 Hz), −122.42 (d, J=229.8 Hz).

$^{13}$C NMR (400 MHz, CDCl$_3$) δ 177.95, 134.39, 131.83, 129.37, 49.06, 41.10, 40.18, 39.11, 38.57, 29.95, 27.27, 16.64.

LCMS m/z (ESI): 246.2 [M+1]$^+$.

HPLC (ELSD) 99.72%.

Example 10. Preparation of Compound 10

Step 1: At room temperature, Intermediate 4-1 (2 g, 6.6 mmol) was added to ethanol (15 mL), and ammonium chloride (1.76 g, 33 mmol), iron powder (1.84 g, 33 mmol), and water (7.5 mL) were sequentially added. After the addition, the temperature was raised to 90° C. to carry out a reaction for 6 hours. The mixture was cooled to room temperature, filtered, and rotary-dried under reduced pressure. 100 mL water was added and the mixture was extracted 3 times with 200 ml dichloromethane. The organic layer was dried over anhydrous sodium sulfate, and the organic solvent was rotary-evaporated under reduced pressure, to give 10B (1.45 g, yield 97%) as a white solid.

LC-MSm/z (ESI): 228.1[M+1]$^+$.

Step 2: Compound 10B (1.3 g, 5.7 mmol) was added to a 10 mL sodium hydroxide solution (6 mol/L) to carry out a reaction under reflux for 12 hours. The reaction solution was concentrated, 20 mL water was added, and the mixture was extracted twice with 20 mL dichloromethane. The aqueous phase was adjusted to a pH of about 7 with 6 mol/L HCl, and a large amount of white solid was formed, which was filtered to give Compound 10 as a white solid (0.57 g, yield 40.7%).

$^1$H NMR (400 MHz, MeOD) δ 3.2-3.08 (m, 2H), 2.84 (s, 1H), 2.68-2.45 (m, 3H), 2.41 (s, 1H), 2.38-2.27 (m, 1H), 2.27-2.06 (m, 2H), 1.97-1.67 (m, 3H), 1.60 (d, 1H).

$^{19}$F NMR (400 MHz, CDCl$_3$) (5-100.91 (d, J=229.8 Hz), −122.41 (d, J=229.8 Hz).

$^{13}$C NMR (400 MHz, CDCl$_3$) δ 178.04, 134.41, 131.90, 129.39, 49.03, 41.09, 40.17, 39.10, 38.58, 29.96, 27.30, 16.65.

LCMS m/z (ESI): 246.1 [M+1]$^+$.

HPLC (ELSD): 98.67%.

Example 11. Preparation of Compound 11

Step 1: At 25° C., ammonium chloride (3.4 g, 0.064 mol), iron (3.6 g, 0.064 mol), and water (10 mL) were added to a solution of Intermediate 5-1 (3.6 g, 0.013 mol) in ethanol (20 ml), followed by stirring at 90° C. for 6 hours. The reaction solution was filtered, and the filtrate was concentrated and poured to water (100 ml). The mixture was extracted with dichloromethane (3×200 ml). The organic phases were combined, dried over anhydrous sodium sulfate, and concentrated to give a crude product, which was 11B (2.6 g, 99%) as a white solid. The crude product was directly used in the next step without purification.

MSm/z (ESI): 204.1 [M+1].

Step 2: Sodium hydroxide (10 ml, 6 mol/L) was added to a solution of 11B (1.3 g, 6.39 mmol) in methanol (10 ml) to carry out a reaction under reflux for 10 hours. The reaction solution was concentrated, water (20 mL) was added, and the mixture was washed with dichloromethane (20 ml*2). The aqueous phase was adjusted to a pH of 7-8 with HCl (6 mol/L), and a large amount of white solid was precipitated, which was filtered. The filter cake was washed with water (10 ml*2) and concentrated to give Compound 11 (0.7 g. 49.5%) as a white solid.

$^1$H NMR (400 MHz, MeOD) δ 4.71 (d, 2H), 3.20-3.11 (m, 2H), 3.12-3.03 (m, 1H), 2.67-2.55 (m, 3H), 2.52 (d, 1H), 2.35 (dd, 1H), 2.08 (dt, 1H), 1.93-1.81 (m, 2H), 1.77 (d, 1H), 1.60-1.50 (m, 2H).

13C NMR (101 MHz, MeOD) δ 180.01 (s, 1H), 156.38 (s, 1H), 104.14 (s, 1H), 51.17 (s, 1H), 45.96 (s, 1H), 43.62 (s, 1H), 43.35 (s, 1H), 43.26 (s, 1H), 42.19 (s, 1H), 41.98 (s, 1H), 35.26 (s, 1H), 33.17 (s, 1H), 20.06 (s, 1H).

MS m/z (ESI): 222.1[M+1].

Example 12. Preparation of Compound 12

Step 1: At 25° C., ammonium chloride (3.4 g, 0.064 mol), iron powder (3.6 g, 0.064 mol), and water (10 mL) were added to a solution of Intermediate 5-2 (3.6 g, 0.013 mol) in ethanol (20 ml), followed by stirring at 90° C. for 6 hours. The reaction mixture was filtered, and the filtrate was concentrated and poured to water (100 ml). The mixture was extracted with dichloromethane (3×200 ml). The organic phases were combined, dried over anhydrous sodium sulfate, and concentrated to give a crude product, which was 12B (2.6 g, 99%) as a white solid. The crude product was directly used in the next step without purification.

MSm/z (ESI): 204.1 [M+1].

Step 2: Sodium hydroxide (10 ml, 6 mol/L) was added to a solution of 12B (1.3 g, 6.39 mmol) in methanol (10 ml), and the mixture was refluxed for 10 hours. The reaction mixture was concentrated, water (20 mL) was added, and the mixture was washed with dichloromethane (20 ml*2). The aqueous phase was adjusted to a pH of 7-8 with HCl (6 mol/L), and a large amount of white solid was precipitated, which was filtered. The filter cake was washed with water (10 ml*2) and concentrated to give Compound 12 (0.65 g. 45.9%) as a white solid.

$^1$H NMR (400 MHz, MeOD) δ 4.71 (d, 2H), 3.17 (d, 2H), 3.12-3.03 (m, 1H), 2.60 (dq, 3H), 2.52 (d, 1H), 2.39-2.30 (m, 1H), 2.08 (dt, 1H), 1.92-1.81 (m, 2H), 1.77 (d, 1H), 1.55 (dt, 2H).

$^{13}$C NMR (101 MHz, MeOD) δ 180.01 (s, 1H), 156.38 (s, 1H), 104.15 (s, 1H), 51.18 (s, 1H), 45.96 (s, 1H), 43.63 (s, 1H), 43.35 (s, 2H), 43.26 (s, 1H), 42.20 (s, 1H), 41.99 (s, 1H), 35.27 (s, 1H), 33.18 (s, 1H), 20.07 (s, 1H).

MS m/z (ESI): 222.1[M+1].

Example 13. Preparation of Compound 13

Step 1: Intermediate 6-1 (0.30 g, 1.0 mmol), ethanol (32 mL), water (16 mL), iron powder (0.57 g, 10.0 mmol) and ammonium chloride (0.22 g, 4.1 mmol) were added to a reaction flask to carry out a reaction under reflux for 6 hours. After cooling to room temperature, the mixture was filtered and concentrated to remove ethanol, and a 50 ml saturated aqueous solution of sodium chloride was added. The mixture was extracted with dichloromethane (50 ml×3). The organic layers were combined, dried, filtered, concentrated, and purified by silica gel column chromatography (dichloromethane/methanol (v/v)=50:1, 10:1) to give 13b (0.23 g, yield 85%) as a white solid.

NMR (400 MHz, CDCl$_3$) δ 3.14 (d, J=4.5 Hz, 2H), 2.89-2.72 (m, 3H), 2.52-2.42 (m, 1H), 2.35-2.18 (m, 2H), 2.05-1.93 (m, 1H), 1.78-1.68 (m, 1H), 1.64-1.40 (m, 15H), 1.33-1.17 (m, 2H).

Step 2: 13b (0.23 g, 0.87 mmol) and dichloromethane (10 mL) were added to a reaction flask, and trifluoroacetic acid (10 mL) was added dropwise thereto in an ice bath, followed by a reaction at room temperature for 4 hours, and then by concentration under reduced pressure. The residue was dissolved in dichloromethane (50 mL), triethylamine was added until the pH of the solution was 7-8, and the solution was filtered by suction. The filter cake was washed with dichloromethane (20 mL×3) and oven-dried to give Compound 13 (0.12 g, yield: 66%) as a white solid.

$^1$H NMR (400 MHz, MeOD) δ 3.00 (dt, 3H), 2.72 (s, 2H), 2.49 (s, 1H), 2.32 (d, 1H), 2.16 (s, 1H), 2.03 (t, 1H), 1.76 (s, 1H), 1.67 (d, 2H), 1.58-1.46 (m, 2H), 1.47-1.37 (m, 1H), 1.30-1.20 (m, 1H).

Example 14. Preparation of Compound 14

Step 1: Intermediate 6-2 (0.30 g, 1.0 mmol), ethanol (32 mL), water (16 mL), iron powder (0.57 g, 10.0 mmol) and ammonium chloride (0.22 g, 4.1 mmol) were added to a reaction flask to carry out a reaction under reflux for 6 hours. After cooling to room temperature, the mixture was filtered and concentrated to remove ethanol, and a 50 ml saturated aqueous solution of sodium chloride was added. The mixture was extracted with dichloromethane (50 ml×3). The organic layers were combined, dried, filtered, concentrated, and purified by silica gel column chromatography (dichloromethane/methanol (v/v)=50:1, 10:1) to give 14b (0.18 g, yield 67%) as a white solid.

Step 2: 14b (0.18 g, 0.68 mmol) and dichloromethane (10 mL) were added to a reaction flask, and trifluoroacetic acid (10 mL) was added dropwise thereto in an ice bath, followed by a reaction at room temperature for 4 hours, and then by concentration under reduced pressure. The residue was dissolved in dichloromethane (50 mL), trimethylamine was added until the pH of the solution was 7-8, and the solution was filtered by suction. The filter cake was washed with dichloromethane (20 mL×3) and oven-dried to give Compound 14 (0.09 g, yield: 63%) as a white solid.

$^1$H NMR (400 MHz, MeOD) δ 3.07-2.90 (m, 3H), 2.72 (s, 2H), 2.54-2.45 (m, 1H), 2.32 (dd, 1H), 2.21-2.11 (m, 1H), 2.04 (dd, 1H), 1.82-1.70 (m, 1H), 1.63 (ddd, J=15.2, 11.2, 6.5 Hz, 1H), 1.57-1.46 (m, 1H), 1.42 (dd, 1H), 1.30-1.22 (m, 1H).

Biological Tests

Test on Competitive Binding Ability of the Compounds to Calcium Channel Protein Cavα2δ

The cerebral cortex of rats was harvested in a 10-fold volume (w/v) of ice-cold 0.32 M sucrose/5 mM Tris-acetic acid (pH 7.4) and homogenized. The synaptic plasma membrane was prepared by sucrose density gradient centrifugation, and preserved in a Tris-acetic acid (pH 7.4) buffer, which was resuspended in a 10 mM HEPES (pH 7.4) buffer immediately before use. The test compounds were each dissolved in 1% DMSO and prepared into serial dilutions (1 nM to 1000 nM), which were added to the suspension of synaptic plasma membrane (approximately 0.05 to 0.1 mg total protein) together with 20 nM [$^3$H] gabapentin, followed by incubation at 25° C. for 30 minutes. After the reaction was completed, the reaction system was vacuum-filtered against a Whatman GFB filter membrane. The filter membrane was then washed three times with 5 mL 100 mM ice-cold sodium chloride solutions, and the radioactivity of the filter membrane was determined by liquid scintillation counting. Non-specific binding was blocked with 100 M gabapentin. The inhibition of the binding of radiolabeled gabapentin to the synaptic plasma membrane by the test compounds was calculated and the $IC_{50}$ of the compounds was calculated. The experimental results are shown in Table 1.

TABLE 1

$IC_{50}$ of the test compounds

| Example No. | $IC_{50}$ (nM) |
|---|---|
| 1 | 9.17 |
| 4 | 10.7 |
| 6 | 20 |
| 7 | 53 |

Conclusion: the compounds of the present invention showed excellent competitive binding ability to the calcium channel protein Cavα2δ.

L5-L6 Spinal Nerve Ligation (SNL) Animal Model

In an environment for animal operations, 6-7 week old SD male rats (purchased from Vital River Laboratory) were anesthetized with 5% isoflurane. The anesthetized animals were placed in a prone position, and incised at the 5th lumbar vertebrae, at which the incision was opened to expose the left paravertebral muscle which was teared layer by layer to expose the L5 and L6 spinal nerves. The distal ends of the L5 and L6 dorsal root ganglia were ligated with a 4-0 surgical wire. The muscles and skin were sutured layer by layer and the animals were allowed to recover for one week.

After the model animals recovered, the contact pain of the animals was tested with Von Frey hairs (DanMic Global; USA). The "up and down" method was used to measure the force exerted by animals upon 50% paw withdrawal threshold (g; 50% PWT). Animals having 50%-PWT force of 1-5 g were enrolled first. Baseline values of the animals were measured before administration of the compounds, followed by oral administration of different compounds (formulated with 5% sodium carboxymethylcellulose), and the pain response of the animals at different time points was tested in the test range of 1.0 g to 15 g. The experimental results are shown in FIG. 1.

Conclusion: as shown in the experimental results, the compounds of the present invention can significantly suppress mechanical hyperalgesia caused by spinal nerve ligation in rats.

Pharmacokinetic Evaluation

Male SD rats (purchased from Vital River Laboratory Animal Technology Co., Ltd.), each weighing 180 to 240 g, were fasted overnight but allowed access to water. Three rats were administered by oral gavage at a dose of 10 mg/kg, and three rats were intravenously injected at 5 mg/kg. For the oral administration group, the compounds were formulated into 1.0 mg/mL suspensions with a 0.5% methylcellulose (MC) solution, and 200 μl blood was sampled before administration and 30 min, 1 h, 2 h, 4 h, 6 h, 8 h, 12 h and 24 h after administration. For the intravenous injection (I.V.) group, the compounds were formulated into 1.0 mg/ml solutions with physiological saline, and blood was sampled before administration and 5 min, 15 min, 30 min, 1 h, 2 h, 4 h, 8 h, 12 h and 24 h after administration. The blood samples were all anticoagulated with heparin, and centrifuged at 5500 rpm for 10 min to collect plasma, which was stored at −20° C. 10 μl plasma of rats for each of the time points was mixed with a 500 μl acetonitrile solution containing an internal standard, vortexed for 10 min, and centrifuged at 3700 rpm for 18 min. 50 μl of the supernatant was mixed with 100 μl water and vortexed for 10 min. 5 μl of the mixture was subjected to an LC-MS/MS analysis to determine the blood drug level of the parent drugs. The main pharmacokinetic parameters were analyzed using the software WinNonlin 6.3 at the non-compartment mode. The experimental results are shown in Table 2.

TABLE 2

Experimental results of pharmacokinetic evaluation in rats

| Example No. | Administration route | Blood Drug Level $C_{max}$ (ng/ml) | Area under curve $AUC_{0-inf}$ (ng/ml · h) | Half-life $t^{1/2}$ (h) | Bio-availability F (%) |
|---|---|---|---|---|---|
| WO2009041453 | Oral | 3853 | 10285 | 2.60 | 83.0 |
| Example 21 | I.V. | N/A | 7828 | 1.90 | N/A |
| 1 | Oral | 3002 | 12898 | 2.30 | 95.0 |
|   | I.V. | N/A | 6799 | 1.30 | N/A |
| 2 | Oral | 3789 | 13473 | 1.40 | 83.0 |
|   | I.V. | N/A | 8147 | 1.40 | N/A |
| 5 | Oral | 4486 | 14207 | 1.60 | 87 |
|   | I.V. | N/A | 8212 | 2.40 | N/A |
| 6 | Oral | 3710 | 13661 | 1.40 | 83.2 |
|   | I.V. | N/A | 8212 | 2.40 | N/A |
| 7 | Oral | 9144 | 22951 | 1.10 | 97.0 |
|   | I.V. | N/A | 11788 | 1.20 | N/A |
| 8 | Oral | 8004 | 25443 | 2.10 | 107.9 |
|   | I.V. | N/A | 11788 | 1.20 | N/A |

Conclusion: The compounds of the present invention displayed excellent pharmacokinetic properties.

The invention claimed is:

1. A compound corresponding to general formula (I), or stereoisomers, solvates, prodrugs, or pharmaceutically acceptable salts thereof,

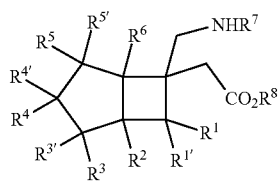

(I)

wherein $R^1$ and $R^4$ bond each other to form $-(CR^9R^{9'})_n-$ or $-CR^9=CR^{9'}-$;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, amino, carboxy, carboxylate, amide group, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl, wherein the alkyl, alkoxy, sulfanyl, alkenyl, alkynyl, carbocyclyl or heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl, and the heterocyclyl contains 1 to 2 heteroatoms selected from N, O or S;

n is selected from 1, 2 or 3;

alternatively, any pair of $R^3$ and $R^{3'}$, $R^5$ and $R^{5'}$, and $R^9$ and $R^{9'}$ forms

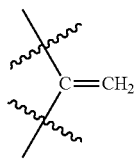

together with the carbon atom to which they are attached, and the

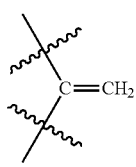

is optionally further substituted with 0 to 2 substituents selected from F, Cl, Br, I, a $C_{1-6}$ alkyl, a 3- to 6-membered carbocyclyl or a 3- to 6-membered heterocyclyl, wherein the alkyl, 3- to 6-membered carbocyclyl or 3- to 6-membered heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl;

alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, amino, a $C_{1-6}$ alkyl, a $C_{1-6}$ alkoxy, or a $C_{1-6}$ sulfanyl;

$R^7$ is selected from H, a $C_{1-6}$ alkyl, or an amino-protecting group; and $R^8$ is selected from H, a $C_{1-6}$ alkyl, or a carboxy-protecting group.

2. The compound according to claim 1, or stereoisomers, solvates, prodrugs, or pharmaceutically acceptable salts thereof, wherein the compound is selected from the compounds corresponding to general formula (Ia) or (Ib):

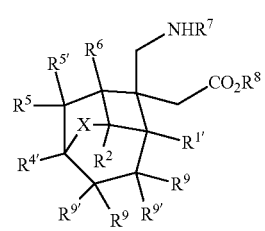

(Ia)

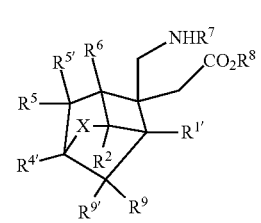

(Ib)

wherein X represents $CR^3R^{3'}$; and the other groups are defined the same as in general formula (I).

3. The compound according to claim 2, or stereoisomers, solvates, prodrugs, or pharmaceutically acceptable salts thereof, wherein $R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, a $C_{1-6}$ alkyl, a $C_{2-6}$ alkenyl, or a $C_{2-6}$ alkynyl, wherein the alkyl, alkenyl, or alkynyl is optionally further substituted with 0 to 6 substituents selected from F, Cl, Br, I, a $C_{1-6}$ alkyl, or a 3- to 6-membered carbocyclyl;

alternatively, any pair of $R^3$ and $R^{3'}$, and $R^9$ and $R^{9'}$ forms

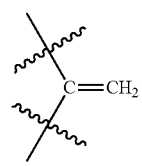

together with the carbon atom to which they are attached;

alternatively, any pair of $R^3$ and $R^{3'}$, and $R^9$ and $R^{9'}$ forms a 3- to 6-membered carbocycle together with the carbon atom to which they are attached;

$R^7$ is selected from H or an amino-protecting group; and $R^8$ is selected from H or a carboxy-protecting group.

4. The compound according to claim 3, or stereoisomers, solvates, prodrugs, or pharmaceutically acceptable salts thereof, wherein $R^{1'}$, $R^2$, $R^3$, $R^{3'}$, $R^{4'}$, $R^5$, $R^{5'}$, $R^6$, $R^9$ or $R^{9'}$ is each independently selected from substituted or unsubstituted H, F, Cl, Br, I, methyl, ethyl, isopropyl, propyl, vinyl, propenyl, ethynyl or propynyl; and when substituted, they are optionally substituted with 1 to 6 substituents selected from F, Cl, Br, I, methyl or ethyl;

alternatively, $R^3$ and $R^{3'}$ together with the carbon atom to which they are attached form

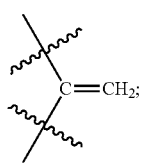
alternatively, $R^3$ and $R^{3'}$ together with the carbon atom to which they are attached form cyclopropyl, cyclobutyl or cyclopentyl;
$R^7$ is H; and $R^8$ is H.
5. The compound according to claim 1, or stereoisomers, solvates, prodrugs, or pharmaceutically acceptable salts thereof, wherein the compound is selected from:
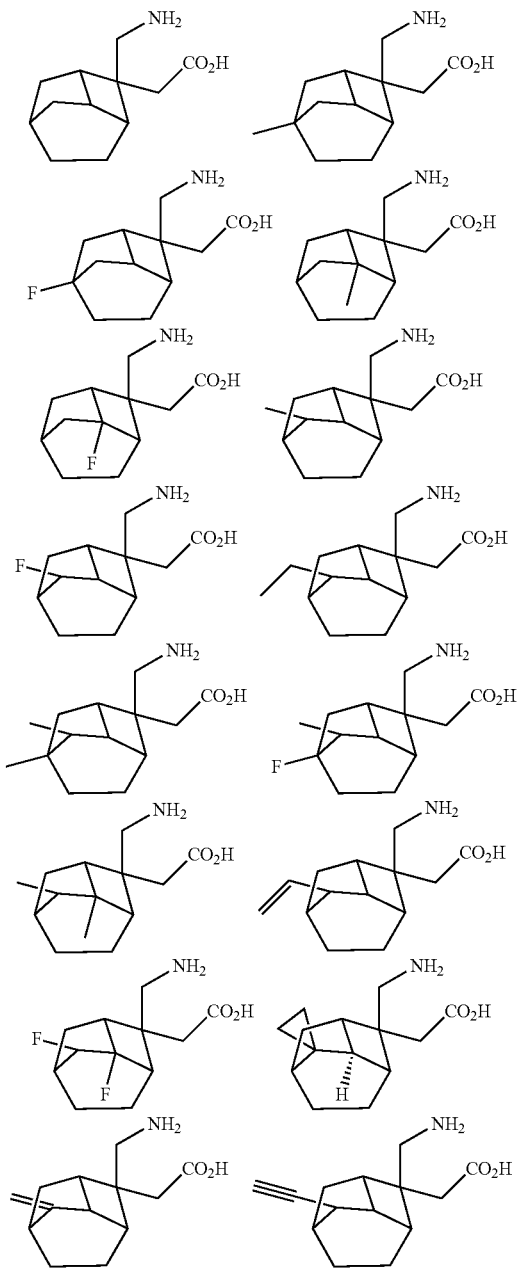
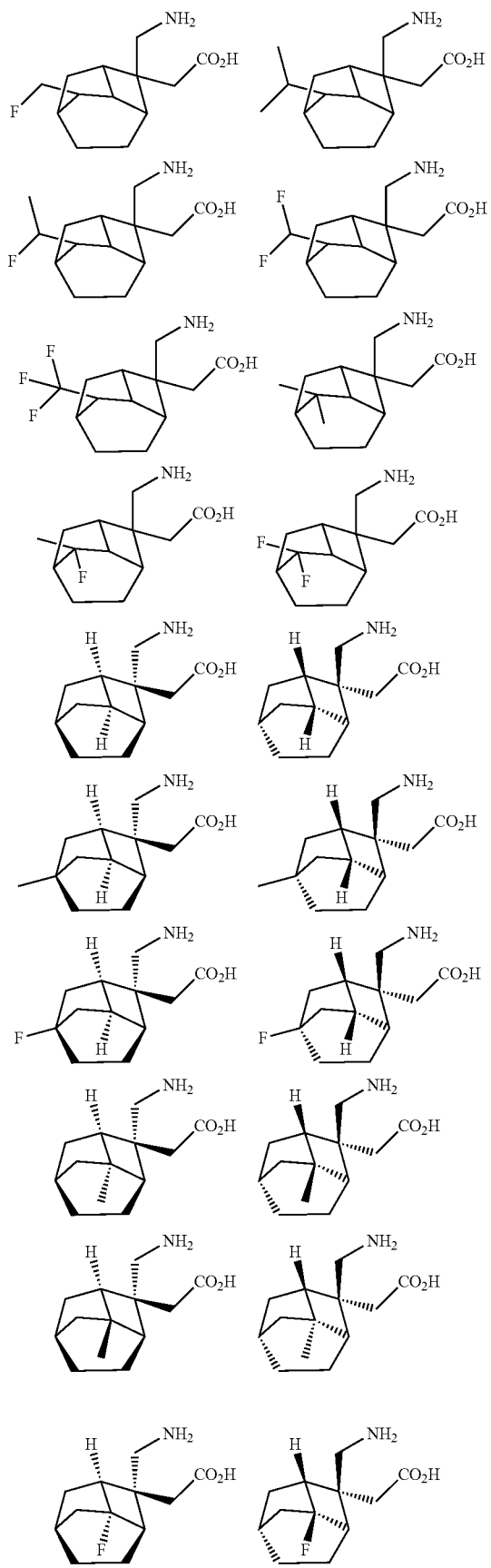

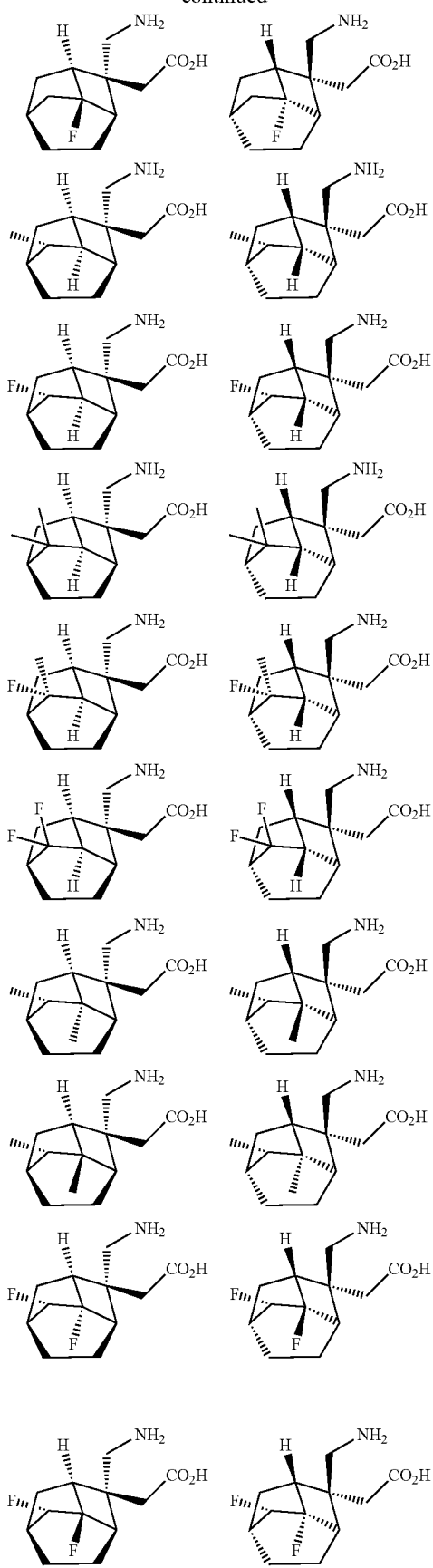
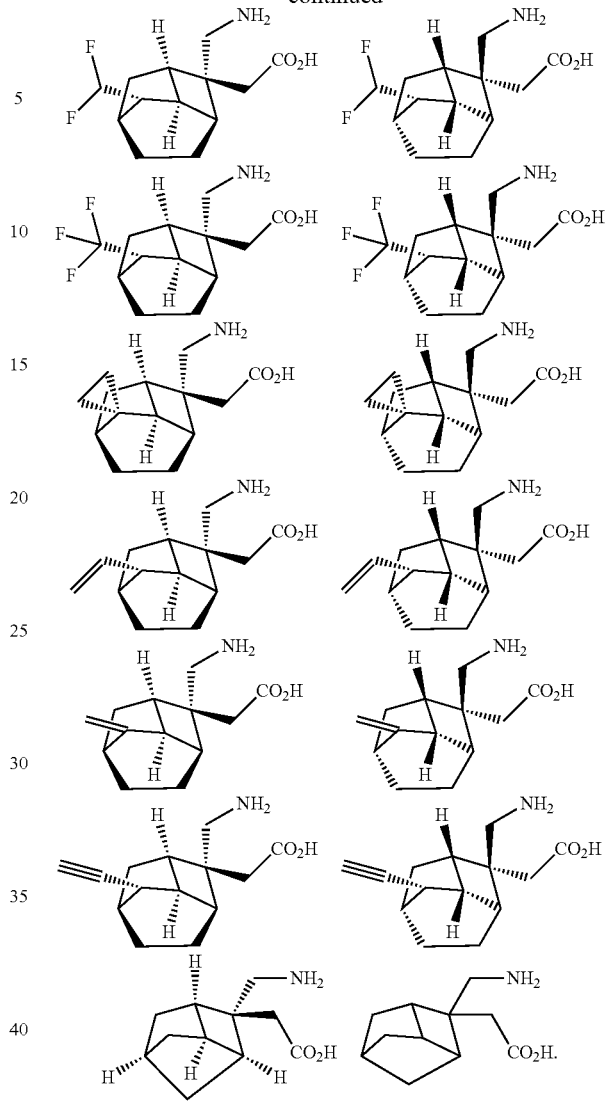

6. The compound according to claim 1, or stereoisomers, solvates, prodrugs, or pharmaceutically acceptable salts thereof, wherein the salts are selected from benzenesulfonate, p-toluenesulfonate or mesylate.

7. A pharmaceutical composition, comprising:
a compound corresponding to general formula (I) or stereoisomers, solvates, pharmaceutically acceptable salts, or prodrugs thereof; and one or more pharmaceutically acceptable carriers and/or excipients;
thereof,

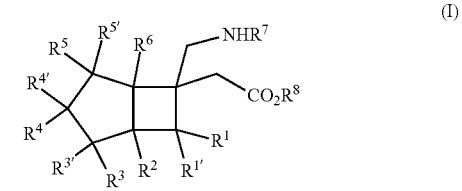

wherein $R^1$ and $R^4$ bond each other to form —$(CR^9R^{9'})_n$— or —$CR^9=CR^{9'}$—;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, amino, carboxy, carboxylate, amide group, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl, wherein the alkyl, alkoxy, sulfanyl, alkenyl, alkynyl, carbocyclyl or heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl, and the heterocyclyl contains 1 to 2 heteroatoms selected from N, O or S;

n is selected from 1, 2 or 3;

alternatively, any pair of $R^3$ and $R^{3'}$, $R^5$ and $R^{5'}$, and $R^9$ and $R^{9'}$ forms

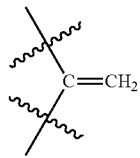

together with the carbon atom to which they are attached, and the

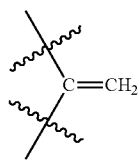 [SMILES: *C(*)=C]

is optionally further substituted with 0 to 2 substituents selected from F, Cl, Br, I, a $C_{1-6}$ alkyl, a 3- to 6-membered carbocyclyl or a 3- to 6-membered heterocyclyl, wherein the alkyl, 3- to 6-membered carbocyclyl or 3- to 6-membered heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl;

alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, amino, a $C_{1-6}$ alkyl, a $C_{1-6}$ alkoxy, or a $C_{1-6}$ sulfanyl;

$R^7$ is selected from H, a $C_{1-6}$ alkyl, or an amino-protecting group; and $R^8$ is selected from H, a $C_{1-6}$ alkyl, or a carboxy-protecting group.

8. A method for treating and/or preventing pain comprising administering the pharmaceutical composition, which comprises one or more pharmaceutically acceptable carriers and/or excipients; and an effective amount of a compound corresponding to general formula (I) or stereoisomers, solvates, pharmaceutically acceptable salts, or prodrugs thereof;

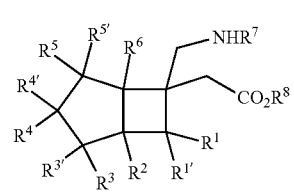

wherein $R^1$ and $R^4$ bond each other to form —$(CR^9R^{9'})_n$- or —$CR^9=CR^{9'}$—;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, amino, carboxy, carboxylate, amide group, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl, wherein the alkyl, alkoxy, sulfanyl, alkenyl, alkynyl, carbocyclyl or heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl, and the heterocyclyl contains 1 to 2 heteroatoms selected from N, O or S;

n is selected from 1, 2 or 3;

alternatively, any pair of $R^3$ and $R^{3'}$, $R^5$ and $R^{5'}$, and $R^9$ and $R^{9'}$ forms

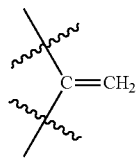 [SMILES: *C(*)=C]

together with the carbon atom to which they are attached, and the

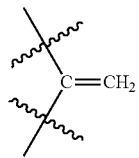

is optionally further substituted with 0 to 2 substituents selected from F, Cl, Br, I, a $C_{1-6}$ alkyl, a 3- to 6-membered carbocyclyl or a 3- to 6-membered heterocyclyl, wherein the alkyl, 3- to 6-membered carbocyclyl or 3- to 6-membered heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl;

alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, amino, a $C_{1-6}$ alkyl, a $C_{1-6}$ alkoxy, or a $C_{1-6}$ sulfanyl;

$R^7$ is selected from H, a $C_{1-6}$ alkyl, or an amino-protecting group; and $R^8$ is selected from H, a $C_{1-6}$ alkyl, or a carboxy-protecting group.

9. The method according to claim 8, wherein the pain is selected from: postherpetic neuralgia, trigeminal neuralgia, migraine, pain associated with osteoarthritis or articular rheumatism, lower back pain, sciatica, toothache, pain caused by burns, pain caused by diabetic neuropathy, pain caused by chemotherapy-induced neuropathy, HIV-related neuralgia, AIDS-related neuralgia, cancer-related neuralgia or non-neuralgia pains, acute or chronic tension headache, postoperative pain, or fibromyalgia.

10. A compound of general formula (Z), or a stereoisomer or a pharmaceutically acceptable salt thereof, wherein:

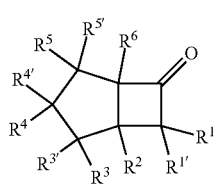
(Z)

$R^1$ and $R^4$ bond each other to form $-(CR^9R^{9'})_n-$ or $-CR^9=CR^{9'}-$;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, hydroxyl, amino, carboxy, carboxylate, amide group, cyano, a $C_{1-6}$ alkyl, a $C_{1-6}$ alkoxy, a $C_{1-6}$ sulfanyl, a $C_{2-6}$ alkenyl, a $C_{2-6}$ alkynyl, a 3- to 6-membered carbocyclyl or a 3- to 6-membered heterocyclyl, wherein the alkyl, alkoxy, sulfanyl, alkenyl, alkynyl, carbocyclyl or heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl, and the heterocyclyl contains 1 to 2 heteroatoms selected from N, O or S;

n is selected from 2 or 3;

alternatively, any pair of $R^3$ and $R^{3'}$, $R^5$ and $R^{5'}$, and $R^9$ and $R^{9'}$ forms

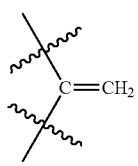 [SMILES: *C(*)=C]

together with the carbon atom to which they are attached, and the

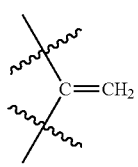

is optionally further substituted with 0 to 2 substituents selected from F, Cl, Br, I, a $C_{1-6}$ alkyl, a 3- to 6-membered carbocyclyl or a 3- to 6-membered heterocyclyl, wherein the alkyl, 3- to 6-membered carbocyclyl or 3- to 6-membered heterocyclyl is optionally further substituted with 0 to 6 substituents selected from F, Cl, Br, I, hydroxyl, amino, carboxy, a $C_{1-6}$ alkyl, a 3- to 6-membered carbocyclyl or a 3- to 6-membered heterocyclyl;

alternatively, any pair of $R^3$ and $R^{3'}$, $R^5$ and $R^{5'}$, and $R^9$ and $R^{9'}$ forms a 3- to 6-membered carbocycle together with the carbon atom to which they are attached, and the carbocycle is optionally further substituted with 0 to 6 substituents selected from F, Cl, Br, I, hydroxyl, amino, a $C_{1-6}$ alkyl, a $C_{1-6}$ alkoxy, or a $C_{1-6}$ sulfanyl;

alternatively, n is 1, $R^3$ and $R^{3'}$ are F, Cl, Br or I, or $R^3$ and $R^{3'}$ form

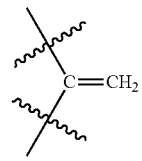 [SMILES: *C(*)=C]

together with the carbon atom to which they are attached, or $R^3$ and $R^{3'}$ form a 3- to 6-membered carbocycle together with the carbon atom to which they are attached.

11. The compound according to claim 10, or a stereoisomer or a pharmaceutically acceptable salt thereof, wherein the compound is selected from the compounds corresponding to general formula (Z-1) or (Z-2):

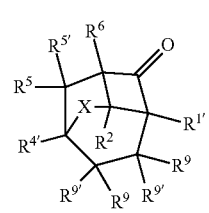
(Z-1)

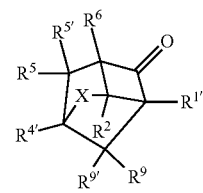
(Z-2)

X represents $CR^3R^{3'}$;

$R^{1'}$, $R^2$, $R^3$, $R^{3'}$, $R^{4'}$, $R^5$, $R^{5'}$, $R^6$, $R^9$ or $R^{9'}$ is each independently selected from H, F, Cl, Br, I, a $C_{1-6}$ alkyl, a $C_{2-6}$ alkenyl, or a $C_{2-6}$ alkynyl, wherein the alkyl, alkenyl, or alkynyl is optionally further substituted with 0 to 6 substituents selected from F, Cl, Br, I, a $C_{1-6}$ alkyl, or a 3- to 6-membered carbocyclyl;

alternatively, any pair of $R^3$ and $R^{3'}$, and $R^9$ and $R^{9'}$ forms

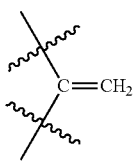

together with the carbon atom to which they are attached;

alternatively, any pair of $R^3$ and $R^{3'}$, and $R^9$ and $R^{9'}$ forms a 3- to 6-membered carbocycle together with the carbon atom to which they are attached;

alternatively, when 12 is 1, $R^3$ and $R^{3'}$ are F, Cl, Br or I, or $R^3$ and $R^{3'}$ form

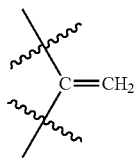

together with the carbon atom to which they are attached, or $R^3$ and $R^{3'}$ form a 3- to 6-membered carbocycle together with the carbon atom to which they are attached.

12. The A pharmaceutical composition according to claim 7, wherein the compound is selected from the compounds corresponding to general formula (Ia) or (Ib):

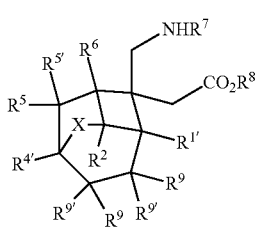 (Ia)

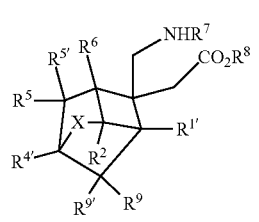 (Ib)

wherein X represents $CR^3R^{3'}$; $R^{1'}$, $R^2$, $R^3$, $R^{3'}$, $R^{4'}$, $R^5$, $R^{5'}$, $R^6$, $R^9$ or $R^{9'}$ is each independently selected from substituted or unsubstituted H, F, Cl, Br, I, methyl, ethyl, isopropyl, propyl, vinyl, propenyl, ethynyl or propynyl; and when substituted, they are optionally substituted with 1 to 6 substituents selected from F, Cl, Br, I, methyl or ethyl;

alternatively, $R^3$ and $R^{3'}$ together with the carbon atom to which they are attached form

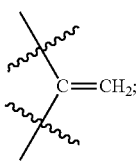

alternatively, $R^3$ and $R^{3'}$ together with the carbon atom to which they are attached form cyclopropyl, cyclobutyl or cyclopentyl;

$R^7$ is H; and $R^8$ is H.

13. The A method according to claim 8, wherein the compound is selected from the compounds corresponding to general formula (Ia) or (Ib):

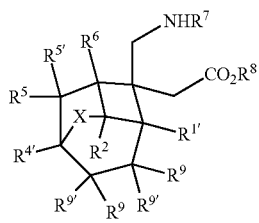 (Ia)

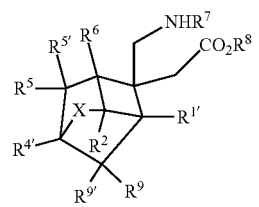 (Ib)

wherein X represents $CR^3R^{3'}$; $R^{1'}$, $R^2$, $R^3$, $R^{3'}$, $R^{4'}$, $R^5$, $R^{5'}$, $R^6$, $R^9$ or $R^{9'}$ is each independently selected from substituted or unsubstituted H, F, Cl, Br, I, methyl, ethyl, isopropyl, propyl, vinyl, propenyl, ethynyl or propynyl; and when substituted, they are optionally substituted with 1 to 6 substituents selected from F, Cl, Br, I, methyl or ethyl;

alternatively, $R^3$ and $R^{3'}$ together with the carbon atom to which they are attached form

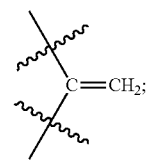

alternatively, $R^3$ and $R^{3'}$ together with the carbon atom to which they are attached form cyclopropyl, cyclobutyl or cyclopentyl;

$R^7$ is H; and $R^8$ is H.

14. The compound according to claim 11, or a stereoisomer or a pharmaceutically acceptable salt thereof, wherein the compound is one selected from:

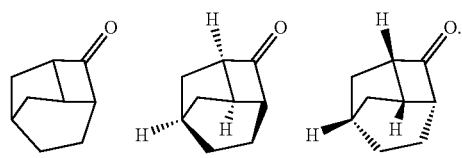

15. The compound according to claim 11, or a stereoisomer or a pharmaceutically acceptable salt thereof, wherein the compound is one selected from:

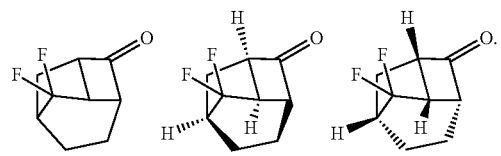

16. The compound according to claim 11, or a stereoisomer or a pharmaceutically acceptable salt thereof, wherein the compound is one selected from:

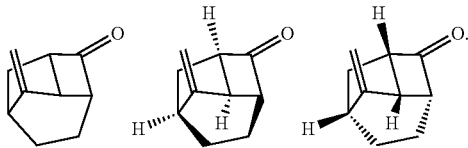

17. The compound according to claim 1, or a stereoisomer or a pharmaceutically acceptable salt thereof, wherein the compound is selected from the compounds corresponding to general formula (Ia) or (Ib):

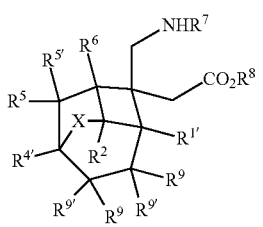
(Ia)

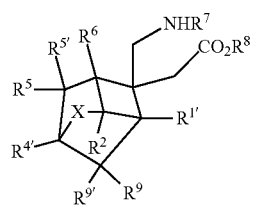
(Ib)

wherein X represents $CR^3R^{3'}$;

$R^{1'}$, $R^2$, $R^3$, $R^{3'}$, $R^{4'}$, $R^5$, $R^{5'}$, $R^6$, $R^9$ or $R^{9'}$ is each independently selected from substituted or unsubstituted H, F, Cl, Br, I, methyl, ethyl, isopropyl, propyl, vinyl, propenyl, ethynyl or propynyl; and when substituted, they are optionally substituted with 1 to 6 substituents selected from F, Cl, Br, I, methyl or ethyl;

alternatively, $R^3$ and $R^{3'}$ together with the carbon atom to which they are attached form

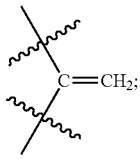 [SMILES: *C(*)=C]

alternatively, $R^3$ and $R^{3'}$ together with the carbon atom to which they are attached form cyclopropyl, cyclobutyl or cyclopentyl;

$R^7$ is H or $C_{1-6}$ alkyl; and $R^8$ is H or $C_{1-6}$ alkyl.

18. The compound according to claim 17, wherein $R^{1'}$, $R^2$, $R^3$, $R^{3'}$, $R^{4'}$, $R^5$, $R^{5'}$, $R^6$, $R^9$ or $R^{9'}$ is each independently selected from H or F;

alternatively, $R^3$ and $R^{3'}$ together with the carbon atom to which they are attached form

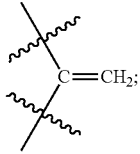 [SMILES: *C(*)=C]

$R^7$ is H or $C_{1-6}$ alkyl; and
$R^8$ is H or $C_{1-6}$ alkyl.

* * * * *